(12) United States Patent
Wixey et al.

(10) Patent No.: US 11,944,302 B2
(45) Date of Patent: Apr. 2, 2024

(54) STAPLE CARTRIDGE FOR A SURGICAL INSTRUMENT

(71) Applicant: INTUITIVE SURGICAL OPERATIONS, INC., Sunnyvale, CA (US)

(72) Inventors: Matthew Wixey, San Jose, CA (US); Atal Patel, Mission Viejo, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 149 days.

(21) Appl. No.: 17/603,252

(22) PCT Filed: Mar. 2, 2020

(86) PCT No.: PCT/US2020/020672
§ 371 (c)(1),
(2) Date: Oct. 12, 2021

(87) PCT Pub. No.: WO2020/214258
PCT Pub. Date: Oct. 22, 2020

(65) Prior Publication Data
US 2022/0183686 A1  Jun. 16, 2022

Related U.S. Application Data

(60) Provisional application No. 62/833,820, filed on Apr. 15, 2019.

(51) Int. Cl.
*A61B 17/072* (2006.01)
*A61B 34/30* (2016.01)

(52) U.S. Cl.
CPC ........ *A61B 17/07207* (2013.01); *A61B 34/30* (2016.02); *A61B 2017/07257* (2013.01);
(Continued)

(58) Field of Classification Search
CPC .... A61B 17/07207; A61B 2017/07257; A61B 2017/07271; A61B 2017/07278;
(Continued)

(56) References Cited

U.S. PATENT DOCUMENTS

| 4,305,539 A | 12/1981 | Korolkov et al. |
| 4,319,576 A | 3/1982 | Rothfuss |

(Continued)

FOREIGN PATENT DOCUMENTS

| EP | 0277532 B1 | 8/1990 |
| EP | 0277529 B1 | 4/1993 |

(Continued)

OTHER PUBLICATIONS

International Search Report and Written Opinion for Application No. PCT/US2021/012284, dated May 6, 2021, 23 pages.

(Continued)

*Primary Examiner* — Stephen F. Gerrity
*Assistant Examiner* — Linda J Hodge
(74) *Attorney, Agent, or Firm* — Farber, LLC

(57) ABSTRACT

The present disclosure provides a staple cartridge for a surgical instrument, such as a tissue sealing instrument. The staple cartridge includes a housing and one or more staple assemblies within the housing. The staple assemblies each include one or more staple pushers and associated staples. The staple pushers and housing include coupling elements configured to cooperate with each other to retain the staple assemblies to the housing prior to use in surgery. The coupling elements, along with other components of the cartridge and instrument, result in a smaller staple cartridge relative to conventional devices, allowing for a more compact and maneuverable surgical instrument.

18 Claims, 16 Drawing Sheets

(52) U.S. Cl.
CPC .............. *A61B 2017/07271* (2013.01); *A61B 2017/07278* (2013.01); *A61B 2034/306* (2016.02)

(58) Field of Classification Search
CPC .............. A61B 34/30; A61B 2034/306; Y10T 403/593; Y10T 403/7092
See application file for complete search history.

(56) References Cited

U.S. PATENT DOCUMENTS

| | | |
|---|---|---|
| 4,407,286 A | 10/1983 | Noiles et al. |
| 4,429,695 A | 2/1984 | Green |
| 4,509,518 A | 4/1985 | McGarry et al. |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,874 A * | 1/1987 | Chow .............. A61B 17/07207 227/176.1 |
| 4,767,044 A | 8/1988 | Green |
| 4,809,695 A | 3/1989 | Gwathmey et al. |
| 4,848,637 A | 7/1989 | Pruit |
| 4,892,244 A | 1/1990 | Fox et al. |
| 4,930,503 A | 6/1990 | Pruit |
| 4,978,049 A | 12/1990 | Green |
| 5,027,834 A | 7/1991 | Pruit |
| 5,040,715 A | 8/1991 | Green et al. |
| 5,133,735 A | 7/1992 | Slater et al. |
| 5,133,736 A | 7/1992 | Bales, Jr. et al. |
| 5,147,357 A | 9/1992 | Rose et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,395 A | 8/1994 | Jarrett et al. |
| 5,342,396 A | 8/1994 | Stein |
| 5,366,133 A | 11/1994 | Geiste |
| 5,452,836 A | 9/1995 | Huitema |
| 5,452,837 A | 9/1995 | Williamson |
| 5,480,089 A | 1/1996 | Blewett |
| 5,484,095 A | 1/1996 | Green |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,564,615 A | 10/1996 | Bishop et al. |
| 5,571,116 A | 11/1996 | Bolanos |
| 5,571,285 A | 11/1996 | Chow |
| 5,573,534 A | 11/1996 | Stone |
| 5,615,820 A | 4/1997 | Viola |
| 5,624,452 A | 4/1997 | Yates |
| 5,628,446 A | 5/1997 | Geiste et al. |
| 5,651,491 A | 7/1997 | Heaton et al. |
| 5,652,849 A | 7/1997 | Conway et al. |
| 5,667,626 A | 9/1997 | Levin |
| 5,673,842 A | 10/1997 | Bittner et al. |
| 5,676,674 A | 10/1997 | Bolanos |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel |
| 5,700,270 A | 12/1997 | Peyser et al. |
| 5,700,276 A | 12/1997 | Benecke |
| 5,709,680 A | 1/1998 | Yates |
| 5,752,644 A | 5/1998 | Bolanos et al. |
| 5,752,973 A | 5/1998 | Kieturakis et al. |
| 5,762,255 A | 6/1998 | Chrisman et al. |
| 5,762,256 A | 6/1998 | Mastri et al. |
| 5,782,396 A | 7/1998 | Mastri et al. |
| 5,792,135 A | 8/1998 | Madhani et al. |
| 5,779,130 A | 10/1998 | Alesi et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman |
| 5,871,135 A | 2/1999 | Williamson, IV et al. |
| 5,911,353 A | 6/1999 | Bolanos et al. |
| 5,915,616 A | 6/1999 | Viola |
| 5,919,198 A * | 7/1999 | Graves, Jr. ....... A61B 17/07207 227/176.1 |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,050,996 A | 4/2000 | Schmaltz et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze |
| 6,953,139 B2 | 10/2005 | Milliman et al. |
| 6,959,852 B2 | 11/2005 | Shelton |
| 6,964,363 B2 | 11/2005 | Wales |
| 6,978,921 B2 | 12/2005 | Shelton |
| 6,978,922 B2 | 12/2005 | Bilotti |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze |
| 7,044,352 B2 | 5/2006 | Shelton, IV et al. |
| 7,044,353 B2 | 5/2006 | Mastri et al. |
| 7,055,731 B2 | 6/2006 | Shelton |
| 7,059,508 B2 | 6/2006 | Shelton |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Shelton, IV et al. |
| 7,140,528 B2 | 11/2006 | Shelton, IV et al. |
| 7,258,262 B2 | 8/2007 | Mastri et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton et al. |
| 7,398,908 B2 | 7/2008 | Holsten |
| 7,401,721 B2 | 7/2008 | Holsten |
| 7,407,075 B2 | 8/2008 | Holsten |
| 7,455,676 B2 | 11/2008 | Holsten |
| 7,472,814 B2 | 1/2009 | Mastri et al. |
| 7,481,349 B2 | 1/2009 | Holsten |
| 7,494,039 B2 | 2/2009 | Racenet et al. |
| 7,565,993 B2 | 7/2009 | Milliman et al. |
| 7,588,174 B2 | 9/2009 | Holsten |
| 7,654,431 B2 | 2/2010 | Hueil et al. |
| 7,658,312 B2 | 2/2010 | Vidal et al. |
| 7,673,783 B2 | 3/2010 | Morgan |
| 7,699,835 B2 | 4/2010 | Lee et al. |
| 7,721,930 B2 | 5/2010 | McKenna |
| 7,726,539 B2 | 6/2010 | Holsten |
| 7,770,774 B2 | 8/2010 | Mastri et al. |
| 7,794,475 B2 | 9/2010 | Hess et al. |
| 7,832,611 B2 | 11/2010 | Boyden |
| 7,837,079 B2 | 11/2010 | Holsten |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten |
| 8,083,118 B2 | 12/2011 | Milliman et al. |

(56) References Cited

U.S. PATENT DOCUMENTS

| | | |
|---|---|---|
| 8,127,975 B2 | 3/2012 | Olson et al. |
| 8,157,152 B2 | 4/2012 | Holsten |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton |
| 8,579,178 B2 | 11/2013 | Holsten |
| 8,608,047 B2 | 12/2013 | Holsten |
| 8,672,939 B2 | 3/2014 | Garrison |
| 8,783,541 B2 | 7/2014 | Shelton |
| 8,800,841 B2 | 8/2014 | Ellerhorst et al. |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 * | 12/2015 | Scheib ................ A61B 17/072 |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,285,693 B2 | 5/2019 | Kimsey et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,642,129 B2 | 5/2023 | Burbank |
| 2002/0165562 A1 | 11/2002 | Grant et al. |
| 2003/0135204 A1 | 7/2003 | Lee et al. |
| 2003/0178465 A1 | 9/2003 | Bilotti |
| 2003/0181910 A1 | 9/2003 | Dycus et al. |
| 2004/0004105 A1 | 1/2004 | Jankowski |
| 2004/0232195 A1 | 11/2004 | Shelton |
| 2004/0232199 A1 | 11/2004 | Shelton |
| 2004/0267310 A1 | 12/2004 | Racenet et al. |
| 2005/0006430 A1 | 1/2005 | Wales |
| 2005/0006431 A1 | 1/2005 | Shelton |
| 2005/0006434 A1 | 1/2005 | Wales |
| 2005/0023324 A1 | 2/2005 | Doll et al. |
| 2005/0070925 A1 | 3/2005 | Shelton |
| 2005/0070958 A1 | 3/2005 | Swayze |
| 2005/0101991 A1 | 5/2005 | Ahlberg et al. |
| 2005/0113826 A1 | 5/2005 | Johnson et al. |
| 2005/0173490 A1 | 8/2005 | Shelton |
| 2005/0178813 A1 | 8/2005 | Swayze |
| 2005/0187576 A1 | 8/2005 | Whitman |
| 2005/0263562 A1 | 12/2005 | Shelton |
| 2005/0273084 A1 | 12/2005 | Hinman et al. |
| 2005/0273085 A1 | 12/2005 | Hinman et al. |
| 2006/0000868 A1 | 1/2006 | Shelton |
| 2006/0016853 A1 | 1/2006 | Racenet |
| 2006/0022014 A1 | 2/2006 | Shelton |
| 2006/0022015 A1 | 2/2006 | Shelton |
| 2006/0024817 A1 | 2/2006 | Ortiz |
| 2006/0025809 A1 | 2/2006 | Shelton |
| 2006/0025810 A1 | 2/2006 | Shelton |
| 2006/0025811 A1 | 2/2006 | Shelton |
| 2006/0025812 A1 | 2/2006 | Shelton |
| 2006/0025813 A1 | 2/2006 | Shelton |
| 2006/0025816 A1 | 2/2006 | Shelton |
| 2006/0097026 A1 | 5/2006 | Shelton |
| 2006/0111209 A1 | 5/2006 | Hinman et al. |
| 2006/0111210 A1 | 5/2006 | Hinman |
| 2006/0161190 A1 | 7/2006 | Gadberry et al. |
| 2006/0190031 A1 | 8/2006 | Wales et al. |
| 2006/0217706 A1 | 9/2006 | Lau et al. |
| 2006/0049230 A1 | 10/2006 | Shelton |
| 2006/0226196 A1 | 10/2006 | Hueil |
| 2007/0010838 A1 | 1/2007 | Shelton |
| 2007/0045379 A1 | 3/2007 | Shelton |
| 2007/0102475 A1 | 5/2007 | Ortiz et al. |
| 2007/0131732 A1 | 6/2007 | Holsten |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0078804 A1 | 4/2008 | Shelton |
| 2008/0086114 A1 | 4/2008 | Schmitz et al. |
| 2009/0277947 A1 | 11/2009 | Viola |
| 2010/0006620 A1 | 1/2010 | Sorrentino et al. |
| 2010/0076474 A1 | 3/2010 | Yates et al. |
| 2010/0108740 A1 | 5/2010 | Pastorelli |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0331857 A1 | 12/2010 | Doyle et al. |
| 2011/0022078 A1 | 1/2011 | Hinman |
| 2011/0118707 A1 | 5/2011 | Burbank |
| 2011/0152879 A1 | 6/2011 | Williams |
| 2011/0174863 A1 | 7/2011 | Shelton et al. |
| 2011/0251612 A1 | 10/2011 | Faller et al. |
| 2011/0251613 A1 | 10/2011 | Guerra et al. |
| 2011/0290851 A1 | 12/2011 | Shelton, IV |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0223121 A1 | 9/2012 | Viola et al. |
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0248577 A1 | 6/2013 | Leimbach |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton et al. |
| 2014/0005653 A1 | 1/2014 | Shelton, IV et al. |
| 2014/0021239 A1 * | 1/2014 | Kostrzewski ......... A61B 90/08 |
| | | 227/175.3 |
| 2014/0025071 A1 | 1/2014 | Sims et al. |
| 2014/0100600 A1 | 4/2014 | Kendrick |
| 2014/0175152 A1 | 6/2014 | Hess et al. |
| 2014/0180286 A1 | 6/2014 | Marczyk et al. |
| 2014/0200596 A1 | 7/2014 | Weir et al. |
| 2014/0214049 A1 | 7/2014 | Jeong et al. |
| 2014/0257331 A1 | 9/2014 | Kim et al. |
| 2014/0263546 A1 | 9/2014 | Aranyi |
| 2014/0263559 A1 | 9/2014 | Williams |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0343550 A1 | 11/2014 | Faller et al. |
| 2014/0343569 A1 | 11/2014 | Turner |
| 2014/0364851 A1 | 12/2014 | Batross et al. |
| 2015/0173789 A1 | 6/2015 | Baxter, III et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0297227 A1 | 10/2015 | Huitema et al. |
| 2015/0297235 A1 | 10/2015 | Harris et al. |

(56) References Cited

U.S. PATENT DOCUMENTS

| | | |
|---|---|---|
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0338764 A1 | 11/2016 | Krastins et al. |
| 2017/0042604 A1 | 2/2017 | McFarland et al. |
| 2017/0079710 A1 | 3/2017 | Deville et al. |
| 2017/0010578 A1 | 4/2017 | Witt et al. |
| 2017/0097035 A1 | 4/2017 | Zimmerman et al. |
| 2017/0135746 A1 | 5/2017 | Tetzlaff et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168622 A1 | 6/2018 | Shelton et al. |
| 2018/0168628 A1 | 6/2018 | Hunter |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168649 A1 | 6/2018 | Shelton, IV et al. |
| 2018/0168650 A1* | 6/2018 | Shelton, IV ............ A61B 34/30 |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310948 A1 | 11/2018 | Stamm et al. |
| 2018/0317915 A1 | 11/2018 | McDonald, II |
| 2019/0000454 A1 | 1/2019 | Swayze et al. |
| 2019/0015124 A1 | 1/2019 | Williams et al. |
| 2019/0059894 A1 | 2/2019 | Kumada et al. |
| 2019/0083086 A1 | 3/2019 | Klaffenböck et al. |
| 2019/0099181 A1 | 4/2019 | Shelton, IV et al. |
| 2019/0125347 A1 | 5/2019 | Stokes et al. |
| 2019/0142531 A1 | 5/2019 | Wentworth et al. |
| 2019/0167266 A1 | 6/2019 | Patel et al. |
| 2019/0201146 A1 | 7/2019 | Shelton, IV et al. |
| 2019/0231350 A1 | 8/2019 | Scott et al. |
| 2019/0239881 A1 | 8/2019 | Laurent et al. |
| 2019/0290374 A1 | 9/2019 | Ramadorai |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0267596 A1* | 9/2021 | Fanelli .................. A61B 34/30 |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0192665 A1 | 6/2022 | Wellman |
| 2022/0346790 A1 | 11/2022 | Wellman |
| 2022/0378537 A1 | 12/2022 | Hites et al. |
| 2022/0395270 A1 | 12/2022 | Patel et al. |
| 2023/0020577 A1 | 1/2023 | Kerver et al. |
| 2023/0047784 A1 | 2/2023 | Patel et al. |
| 2023/0052074 A1 | 2/2023 | Wixey |

FOREIGN PATENT DOCUMENTS

| | | |
|---|---|---|
| EP | 0641546 A1 | 3/1995 |
| EP | 1090592 | 4/2001 |
| EP | 1728473 | 12/2006 |
| EP | 1479346 | 1/2007 |
| EP | 1 621 141 | 7/2007 |
| EP | 1316290 | 2/2012 |
| EP | 1754445 | 10/2013 |
| EP | 3135225 | 3/2017 |
| EP | 3158947 A1 | 4/2017 |
| EP | 3173029 A1 | 5/2017 |
| FR | 2828952 | 12/2005 |
| JP | 5301166 | 9/2008 |
| JP | 2014530653 A | 11/2014 |
| JP | 2016513570 A | 5/2016 |
| JP | 6411461 | 6/2016 |
| JP | 2017500146 A | 1/2017 |
| JP | 2017513564 A | 6/2017 |
| JP | 2016/508792 | 6/2018 |
| JP | 2017/527396 | 10/2018 |
| JP | 2019141659 A | 8/2019 |
| SU | 405234 | 9/1975 |
| SU | 886900 | 12/1981 |
| SU | 1333319 | 12/1985 |
| SU | 1442191 | 12/1988 |
| SU | 1459659 | 2/1989 |
| WO | WO 86/02254 | 4/1986 |
| WO | WO 90/05489 | 5/1990 |
| WO | WO 97/34533 | 9/1997 |
| WO | WO 03/094743 | 11/2003 |
| WO | WO 03/094746 | 11/2003 |
| WO | WO 03/094747 | 11/2003 |
| WO | WO-2012142872 A1 | 10/2012 |
| WO | WO-2014106275 A1 | 7/2014 |
| WO | WO 2017-034803 | 2/2017 |
| WO | WO-2017026141 A1 | 2/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |

OTHER PUBLICATIONS

International Search Report and Written Opinion for Application No. PCT/US2020/054568, dated Jan. 29, 2021, 13 pages.

International Preliminary Report on Patentability for Application No. PCT/US2019/017646, dated Aug. 27, 2020, 10 pages.

International Search Report and Written Opinion for Application No. PCT/US2019/019501, dated May 9, 2019, 8 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2019/019501, dated Sep. 3, 2020, 7 pages.

International Search Report and Written Opinion for Application No. PCT/US19/17646, dated Apr. 16, 2019, 15 pages.

International Search Report and Written Opinion for Application No. PCT/US2019/066513, dated Apr. 21, 2020, 8 pages.

International Search Report and Written Opinion for Application No. PCT/US2019/066530, dated Apr. 21, 2020, 8 pages.

International Search Report and Written Opinion for Application No. PCT/US2019/062344, dated Mar. 23, 2020.

International Search Report and Written Opinion for Application No. PCT/US2019/064861, dated Mar. 30, 2020.

(56) References Cited

OTHER PUBLICATIONS

International Search Report and Written Opinion for Application No. PCT/US2019/062768, dated Mar. 9, 2020.
International Search Report and Written Opinion for Application No. PCT/US2019/056979, dated Dec. 18, 2019.
International Search Report and Written Opinion for Application No. PCT/US2019/066513, dated Apr. 21, 2020.
International Search Report and Written Opinion for Application No. PCT/US2020/020672, dated Jun. 29, 2020.
International Search Report and Written Opinion for Application No. PCT/US2019/066530, dated Apr. 21, 2020.
International Search Report and Written Opinion for Application No. PCT/US2020/033481, dated Sep. 3, 2020.
International Search Report and Written Opinion for Application No. PCT/US2020/025655, dated Jul. 22, 2020.
European Search Report (Corrected version) for Application No. EP19750317.0, dated Mar. 28, 2022, 26 pages.
Partial European Search Report for Application No. EP19757451.0, dated Feb. 2, 2022, 12 pages.
Supplementary European Search Report for Application No. EP19873128.3, dated Jun. 22, 2022, 7 pages.

\* cited by examiner

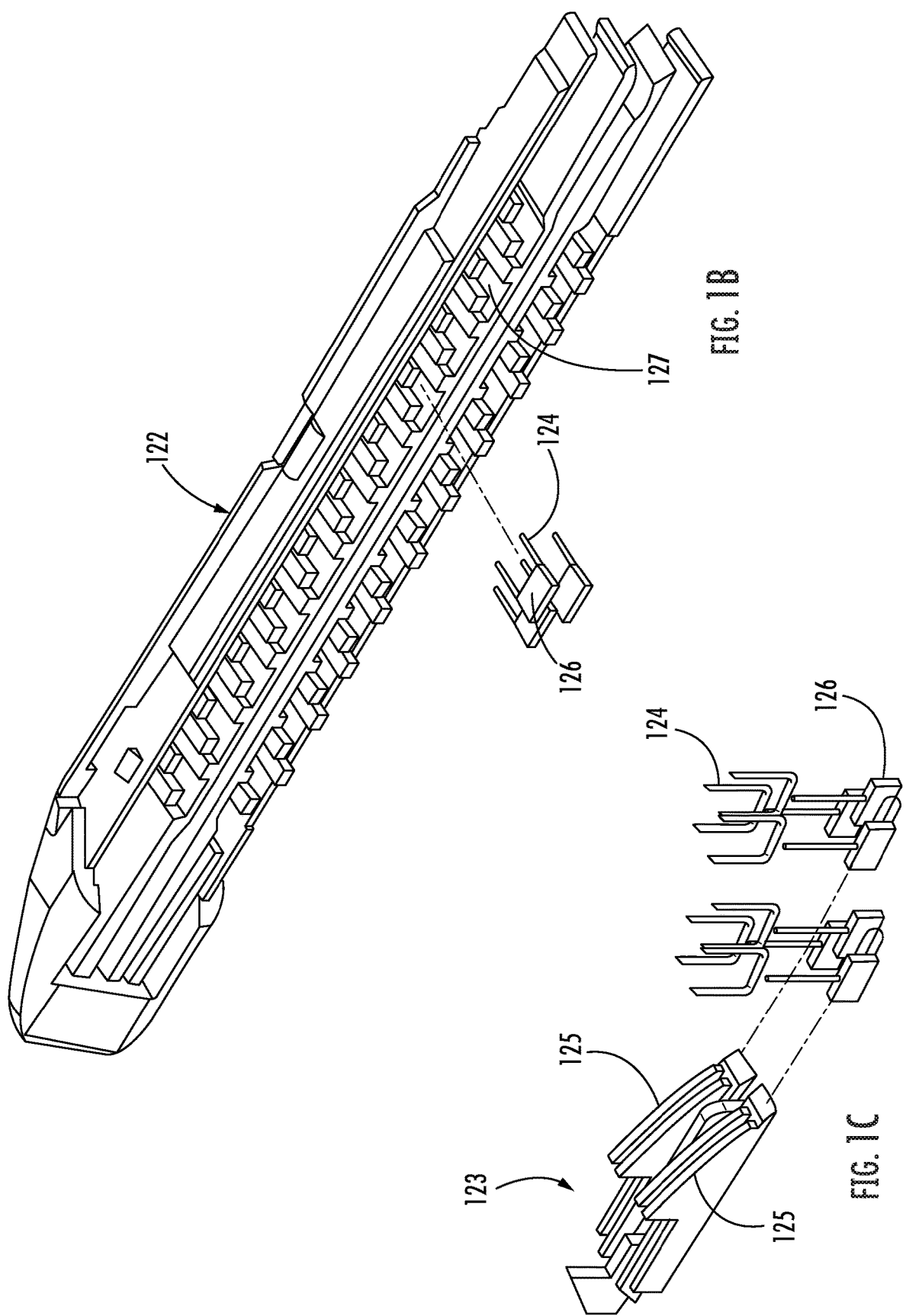

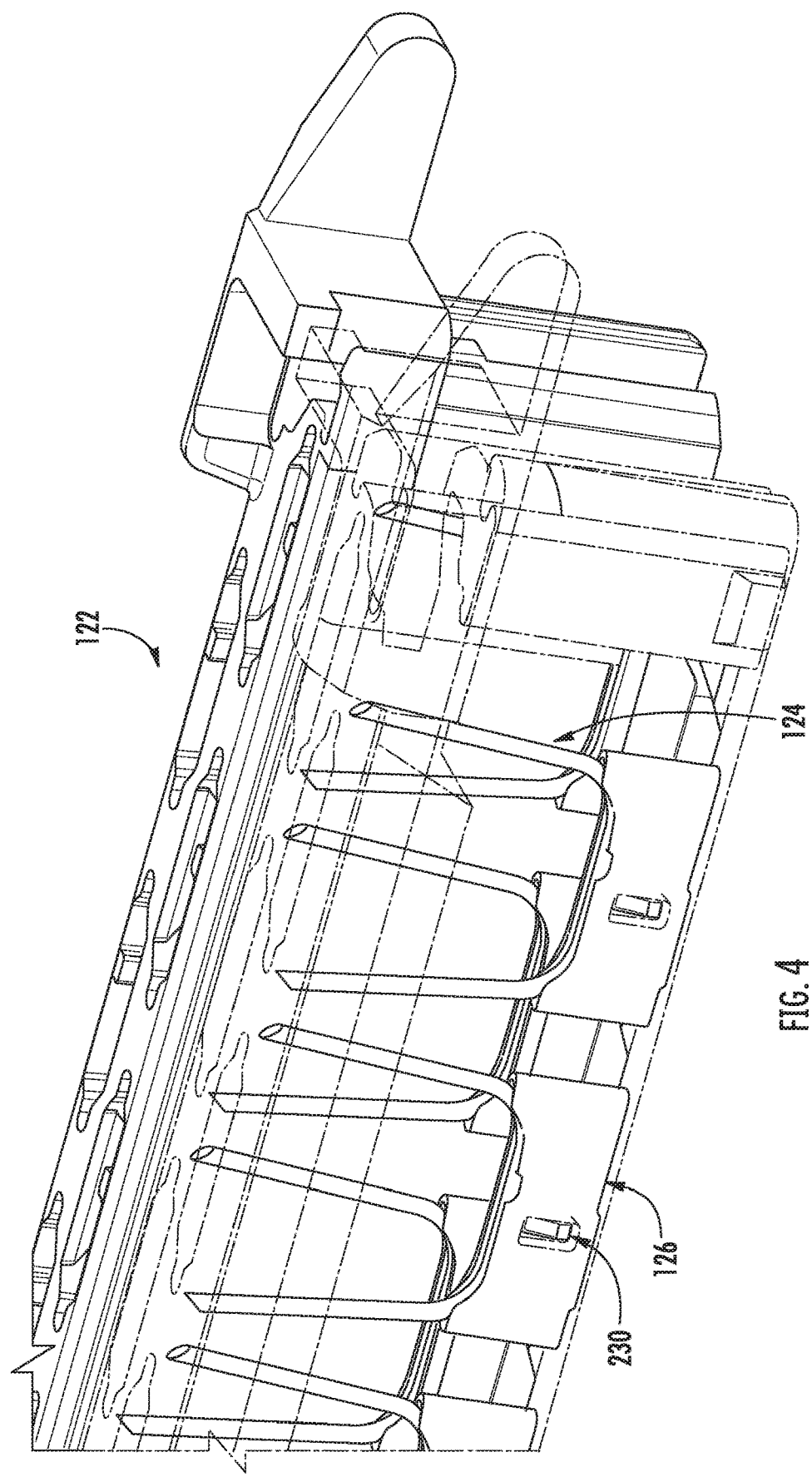

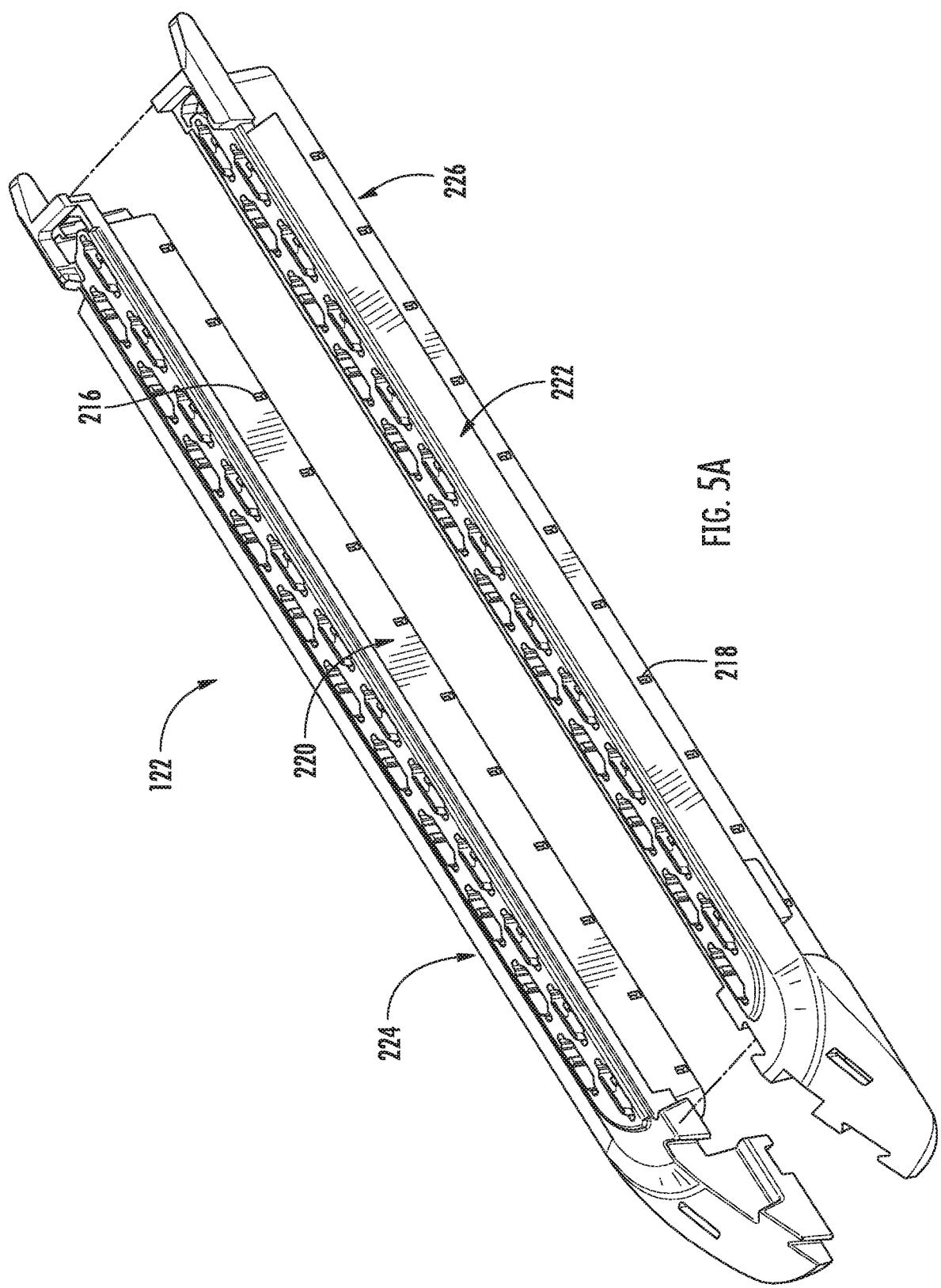

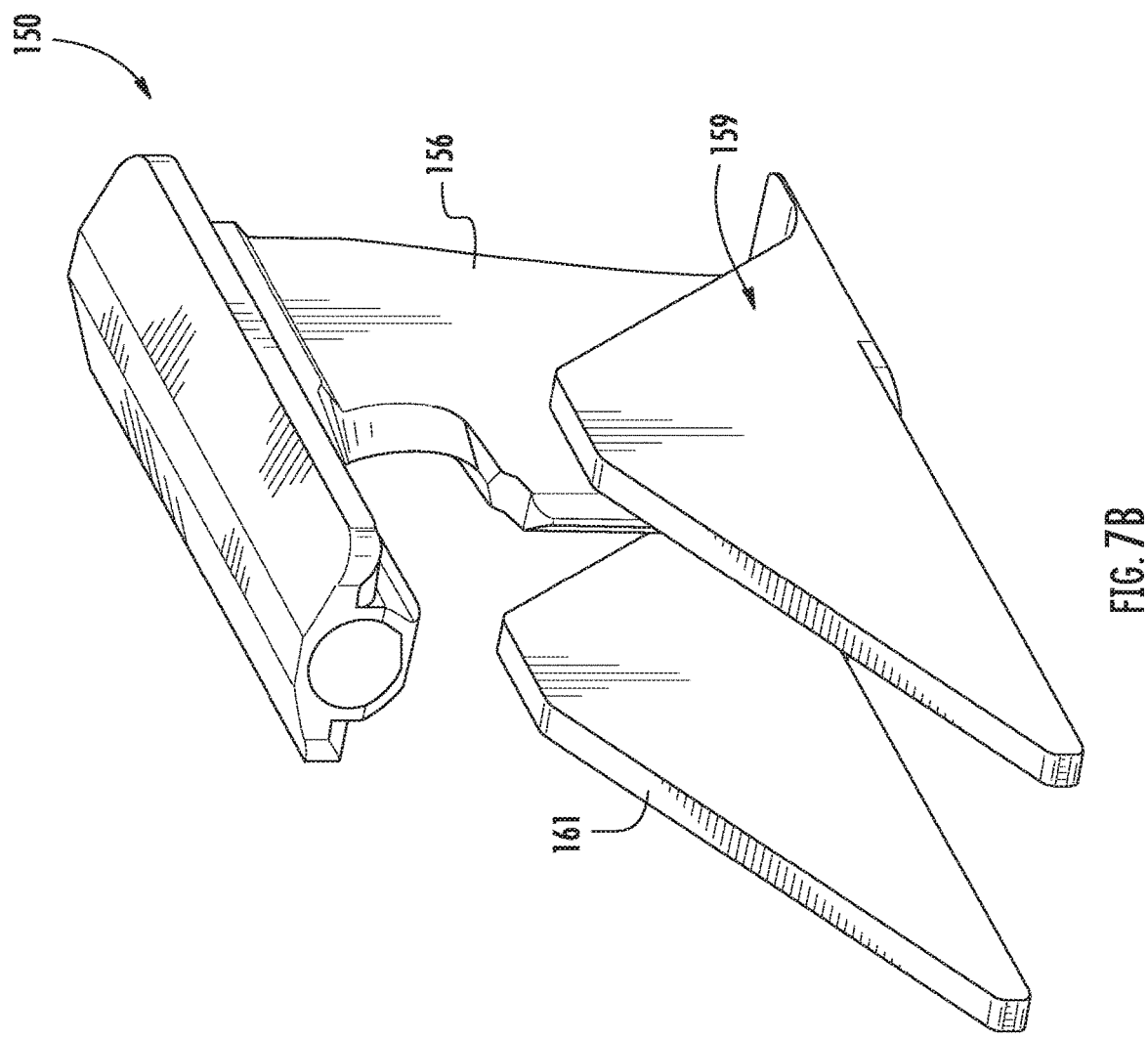
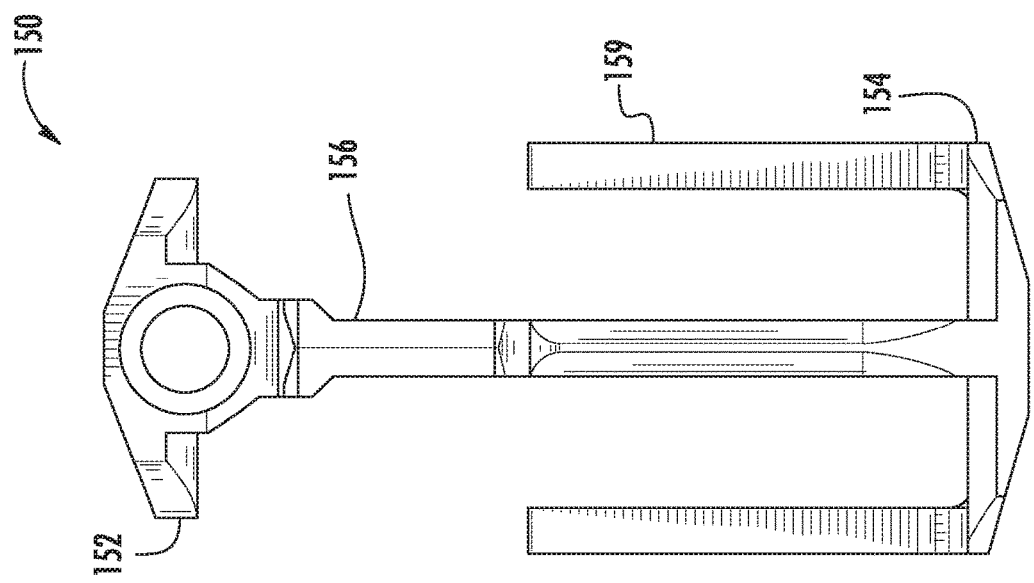

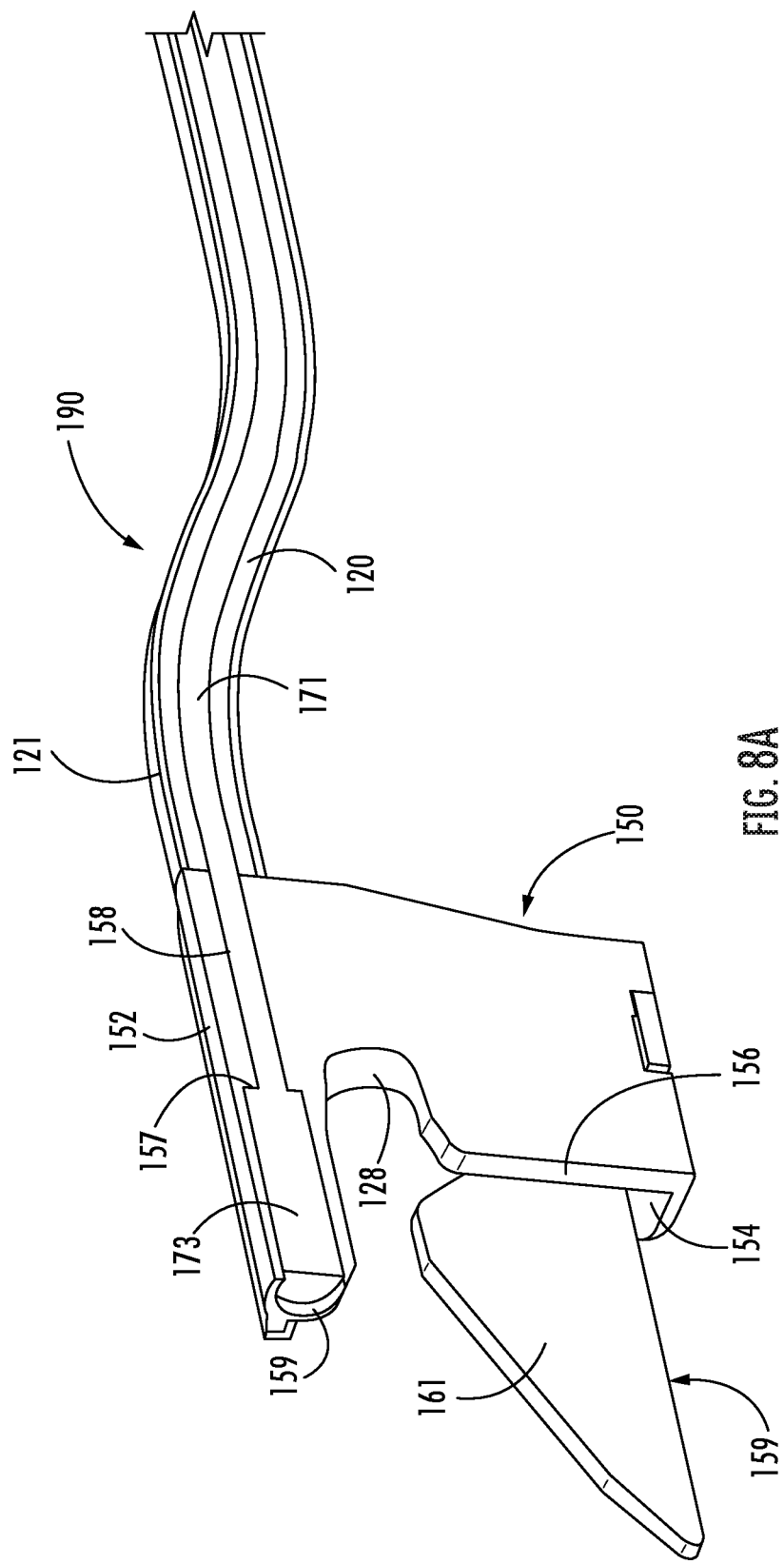

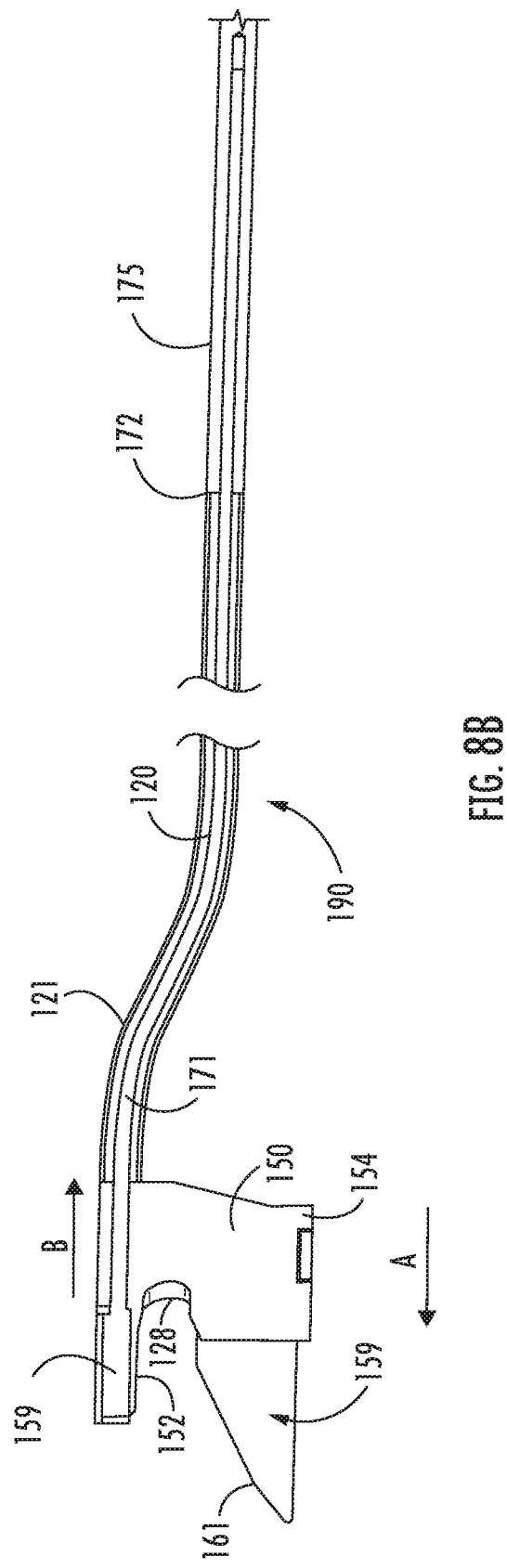

STAPLE CARTRIDGE FOR A SURGICAL INSTRUMENT

CROSS-REFERENCE TO RELATED APPLICATIONS

This application claims the benefit of U.S. Provisional Application Ser. No. 62/833,820, filed Apr. 15, 2019, the entire disclosure of which is incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having a more compact staple cartridge for holding a staple.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. No. 7,594,912 (filed Sep. 30, 2004), U.S. Pat. No. 6,758,843 (filed Apr. 26, 2002), U.S. Pat. No. 6,246,200 (filed Aug. 3, 1999), and U.S. Pat. No. 5,800,423 (filed Jul. 20, 1995), the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. No. 6,702,805 (filed Nov. 9, 2000), U.S. Pat. No. 6,676,669 (filed Jan. 16, 2002), U.S. Pat. No. 5,855,583 (filed Nov. 22, 1996), U.S. Pat. No. 5,808,665 (filed Sep. 9, 1996), U.S. Pat. No. 5,445,166 (filed Apr. 6, 1994), and U.S. Pat. No. 5,184,601 (filed Aug. 5, 1991), the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example; holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure, in addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastrointestinal tract. Many known surgical clamping and cutting devices, including known surgical staplers, have opposing jaws that clamp tissue and an articulated knife to cut the clamped tissue.

Surgical clamping and cutting instruments are often deployed into restrictive body cavities (e.g., through a cannula to inside the pelvis). Accordingly, it is desirable for the surgical clamping and cutting instrument to be both compact and maneuverable for best access to and visibility of the surgical site. Known surgical clamping and cutting instruments, however, may fail to be both compact and maneuverable. For example, known surgical staplers may lack maneuverability with respect to multiple degrees of freedom (e.g., Roll, Pitch, and Yaw) and associated desired ranges of motion.

Conventional surgical clamping and cutting instruments often include a stable cartridge designed to fit within the movable jaw of the end effector. The staple cartridge typically contains multiple rows of staple assemblies that each includes a staple and a staple pusher. The staple pusher holds the staple in place prior to use, and then drives the staple into tissue when the instrument is actuated. The requisite size and shape of the staple cartridge, however, limits the ability of the designer to reduce the size and shape of the overall surgical instrument.

One of the design features of conventional staple cartridges that limits its minimum size is that the staple pushers must be attached to the housing of the staple cartridge prior to use (i.e., during shipping, handling, etc.). At the same time, the staple pusher must be capable of forced movement relative to the staple cartridge during use to drive the staples into tissue. To meet these requirements, conventional staple cartridges often include an outer cover that extends around at least a portion of the cartridge housing to retain the staple pushers within the housing. The cover retains the staple pushers within the cartridge while allowing the requisite freedom of movement during use of the surgical instrument. One of the drawbacks with this outer cover, however, is that it adds material to the overall staple cartridge, thereby increasing the height and diameter of the cartridge and providing a downward limitation on the overall size of the cartridge and the surgical instrument.

Accordingly, while the new telesurgical systems and devices have proven highly effective and advantageous, still further improvements would be desirable. In general, it would be desirable to provide improved surgical instruments that are more compact and maneuverable to enhance the efficiency and ease of use of minimally invasive systems. More specifically, it would be beneficial to create smaller stapler cartridges that will, in turn, allow for the design of even more compact and maneuverable surgical instruments.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides a staple cartridge for a surgical instrument comprising a housing having a plurality of openings spaced from each other along the longitudinal axis of the housing. The staple cartridge further comprises one or more staple assemblies each having at least one staple pusher and a staple for driving the staple into a patient's tissue. The staple pushers each include a projection configured to cooperate with one of the openings in the housing to retain the staple assemblies to the housing. The cooperation of the staple pusher projections with the openings in the housing obviates the need for a staple cartridge cover designed to prevent the staple assemblies from disengaging from the housing before use (e.g., during shipping and handling). Eliminating this cover removes material thickness from the device, allowing for the design of taller staples within a staple cartridge of a given size. Alternatively, this design may allow for staples with conventional heights in a more compact staple cartridge and thus a more compact and maneuverable surgical instrument.

In a preferred embodiment, the staple pusher projections comprise a retention boss having an inclined outer surface or ramp configured to extend through one of the openings of the housing. The boss is configured to retain the staple pushers within the housing. The ramp also preferably allows for forced movement of the staple pusher in only one direction relative to the housing such that, during use, a drive member of the surgical instrument can drive the staple pusher and staples substantially perpendicular to the longitudinal axis of the staple cartridge and into the patient's tissue.

In certain embodiments, the housing of the staple cartridge includes inner and outer walls sections each having a row of openings extending along the longitudinal axis of the housing. The staple cartridge further includes two rows of staple assemblies extending along the inner and outer wall sections of the housing. Each staple assembly comprises at least one staple pusher removably coupled to a staple. In certain embodiments, each stable assembly will include two or three staple pushers and their associated staples. The staple pushers have projections extending laterally therefrom that are aligned with the openings in the wall sections to thus engage the openings and retain the staple pushers to the cartridge.

In another embodiment, the housing is formed from two separate longitudinal sections coupled to each other. Each of the separate longitudinal sections comprises a row of openings for retaining the staple pushers. The longitudinal sections are preferably manufactured separately from each other to facilitate formation of the openings during, for example, an injection molding process. The longitudinal sections each include a coupling element, preferably formed on a distal portion of the sections. The respective coupling elements cooperate with each other to attach the two longitudinal sections together and form the cartridge. In an exemplary embodiment, the coupling sections including mating elements to align the sections to each other and coupling elements sized and configured to form an interference fit that locks the distal portion of the two longitudinal sections together.

In another aspect of the invention, a surgical instrument in accordance with this disclosure includes an end effector including a first fixed jaw and a second jaw. The second jaw is configured to move relative to the first jaw from an open to a closed position. The surgical instrument further comprises a staple cartridge coupled to one of the first or second jaws. The staple cartridge includes a housing having a plurality of openings spaced from each other along the longitudinal axis of the housing. The staple cartridge further comprises one or more staple assemblies each having at least one staple pusher and a staple for driving the staple into a patient's tissue. One or more of the staple pushers includes a projection configured to cooperate with one of the openings in the housing to retain the staple assemblies to the housing.

In a preferred embodiment, the surgical instrument further includes a drive member configured to translate distally and retract proximally through the end effector. The drive member has a central portion that translates through a channel in the fixed jaw. The central portion may be, for example, a cutting instrument, such as a knife, configured to cut tissue grasped between the first and second jaws when the jaws are in the closed position. The drive member further includes at least one outer portion spaced laterally from the central portion and having an inclined surface or ramp configured to engage the staple assemblies. As the drive member is translated distally, the drive member ramp forces the staple pushers and staples in a perpendicular direction to the longitudinal axis of the housing to drive the staples into tissue. In a particularly preferred embodiment, the central portion and the ramp are integrated into one single drive member that translates through channels formed in the staple cartridge.

In another aspect of the invention, the surgical instrument further includes an actuation mechanism in contact with the central portion of the drive member. The actuation mechanism is configured to advance the drive member distally through the end effector and to retract the drive member proximally through the end effector. In an exemplary embodiment, the actuator includes a control device of a robotic telesurgical system that may, for example, allow for mechanical actuation and control of the surgical instrument to perform a variety of functions, such as grasping a blood vessel; dissecting tissue, or the like, in response to manipulation of master input devices located remotely from the surgical instrument.

In yet another aspect of the invention, a surgical instrument in accordance with this disclosure includes an end effector including a first fixed jaw and a second jaw. The second jaw is configured to move relative to the first jaw from an open to a closed position. The surgical instrument further comprises a staple cartridge coupled to one of the first or second jaws and a drive member configured to translate distally and retract proximally through the end effector. The staple cartridge comprises one or more staple assemblies each having at least one staple pusher removably coupled to a staple. The staple pusher comprises a coupling element configured to retain the staple pusher to the housing, while allowing the drive member to force the staple pusher to move relative to the housing in a direction substantially perpendicular to the longitudinal axis.

In another embodiment, a staple cartridge for a surgical instrument comprises first and second elongated sections each having one or more compartments sized for receiving a staple assembly and a wall extending substantially along a longitudinal axis. The elongated sections each further comprise a plurality of openings spaced from each other along the wall of each section and substantially aligned with the compartments. One or more coupling elements attach the elongated sections together to form the staple cartridge. Preferably, the sections are coupled together such that a first row of the openings resides on the outer section of the cartridge and a second row of the openings resides within the cartridge. This device, in particular, facilitates the formation of the second, inner, row of openings in a standard molding process (e.g., injection molding). After formation, the elongated sections are preferably coupled at their distal ends with one or more coupling elements that create an interference fit, such as a tapered dovetail, snap-fit, press-fit pin or the like.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description serve to explain the principles of the disclosure.

FIG. 1B is a bottom perspective view with parts separated of a representative staple cartridge for an illustrative surgical instrument;

FIG. 1C shows an enlarged view of the cooperative relationship between a portion of a drive member and a plurality of staple pushers and staples which form part of the staple cartridge of FIG. 1B;

FIG. 4 is a semi-transparent view of one portion of a staple cartridge according to certain embodiments of the present disclosure;

FIG. 5A is a perspective top view of two sections of a staple cartridge according to an embodiment of the present disclosure;

FIG. 7A is a front view of a drive member for the illustrative surgical instrument of FIG. 1;

FIG. 7B is a side view of the drive member of FIG. 7A;

FIG. 8A is a partial cross-sectional perspective view of the actuation mechanism for a drive member in accordance with the surgical instrument of FIG. 1;

FIG. 8B is a partial cross-sectional side view of the actuation mechanism for a drive member in accordance with the surgical instrument of FIG. 1;

DETAILED DESCRIPTION

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, wed-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment; the element may nevertheless be claimed as included in the second embodiment. Moreover; the depictions herein are for illustrative purposes only and do not necessarily reflect the actual shape, size, or dimensions of the system or illustrated components.

It is noted that, as used in this specification and the appended claims, the singular forms "a," "an" and "the," and any singular use of any word, include plural referents unless expressly and unequivocally limited to one referent. As used herein; the term "include" and its grammatical variants are intended to be non-limiting, such that recitation of items in a list is not to the exclusion of other like items that can be substituted or added to the listed items.

While the following disclosure is presented with respect to a linear surgical stapler where staples are sequentially fired, it should be understood that the features of the presently described surgical instruments may be readily adapted for use in any type of surgical clamping, cutting, or sealing instruments, whether or not the surgical clamping and cutting instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1:
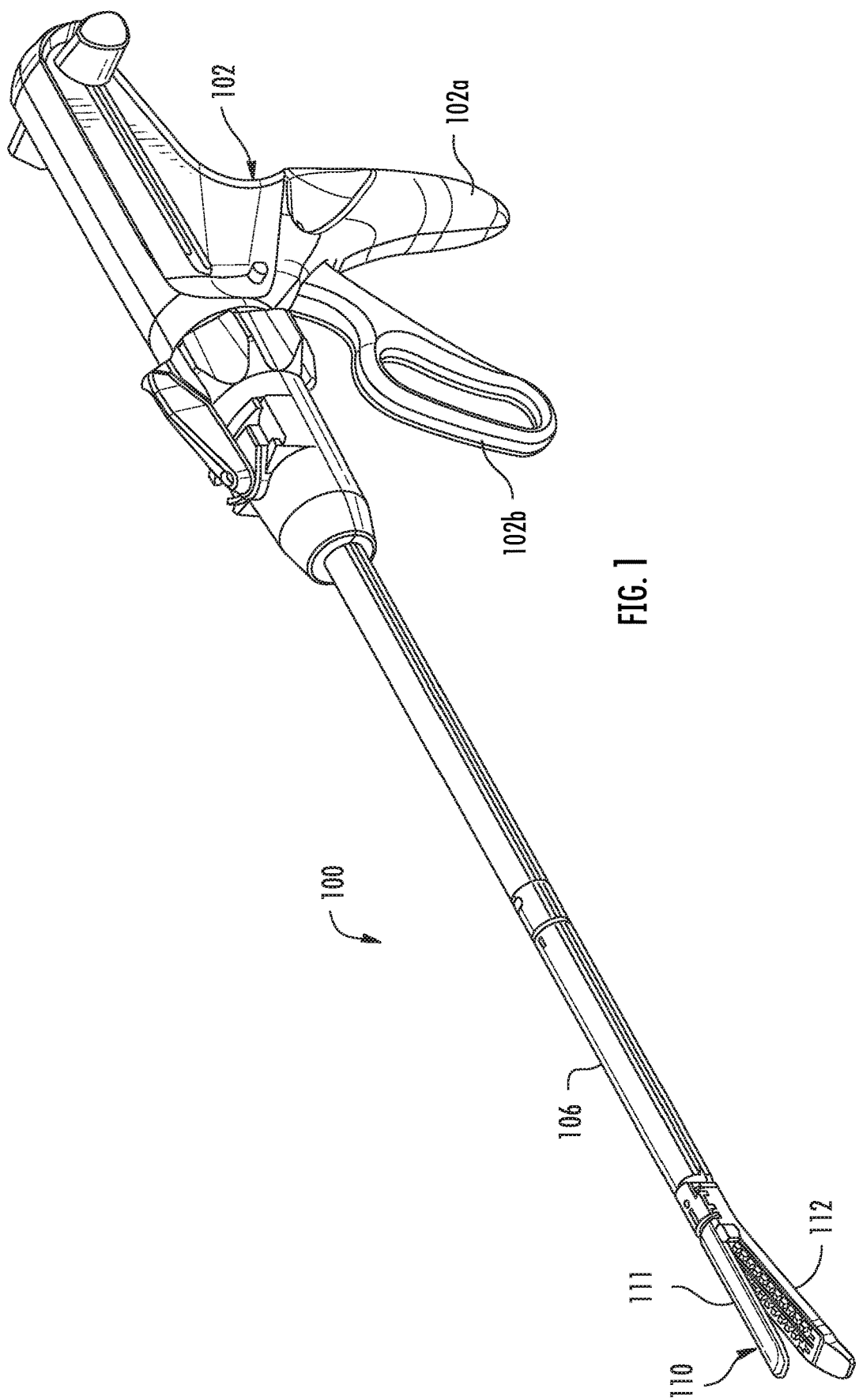
FIG. 1 illustrates a perspective view of an illustrative surgical instrument having an end effector mounted to an elongated shaft.

FIG. 1 is a perspective view of an illustrative surgical instrument 100 in accordance with certain embodiments of the present disclosure having a handle assembly 102, and an end effector 110 mounted on an elongated shaft 106 of the surgical stapling instrument 100. End effector 110 includes a first jaw 111 and a second jaw 112. Handle assembly 102 includes a stationary handle 102a and a moveable handle 102b, which serves as an actuator for surgical instrument 100.

In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S Pub. No. 2014/0183244A1, the entire disclosure of which is incorporated by reference herein. The input couplers are drivingly coupled with one or more input members (not shown) that are disposed within the instrument shaft 106 and end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 1A:
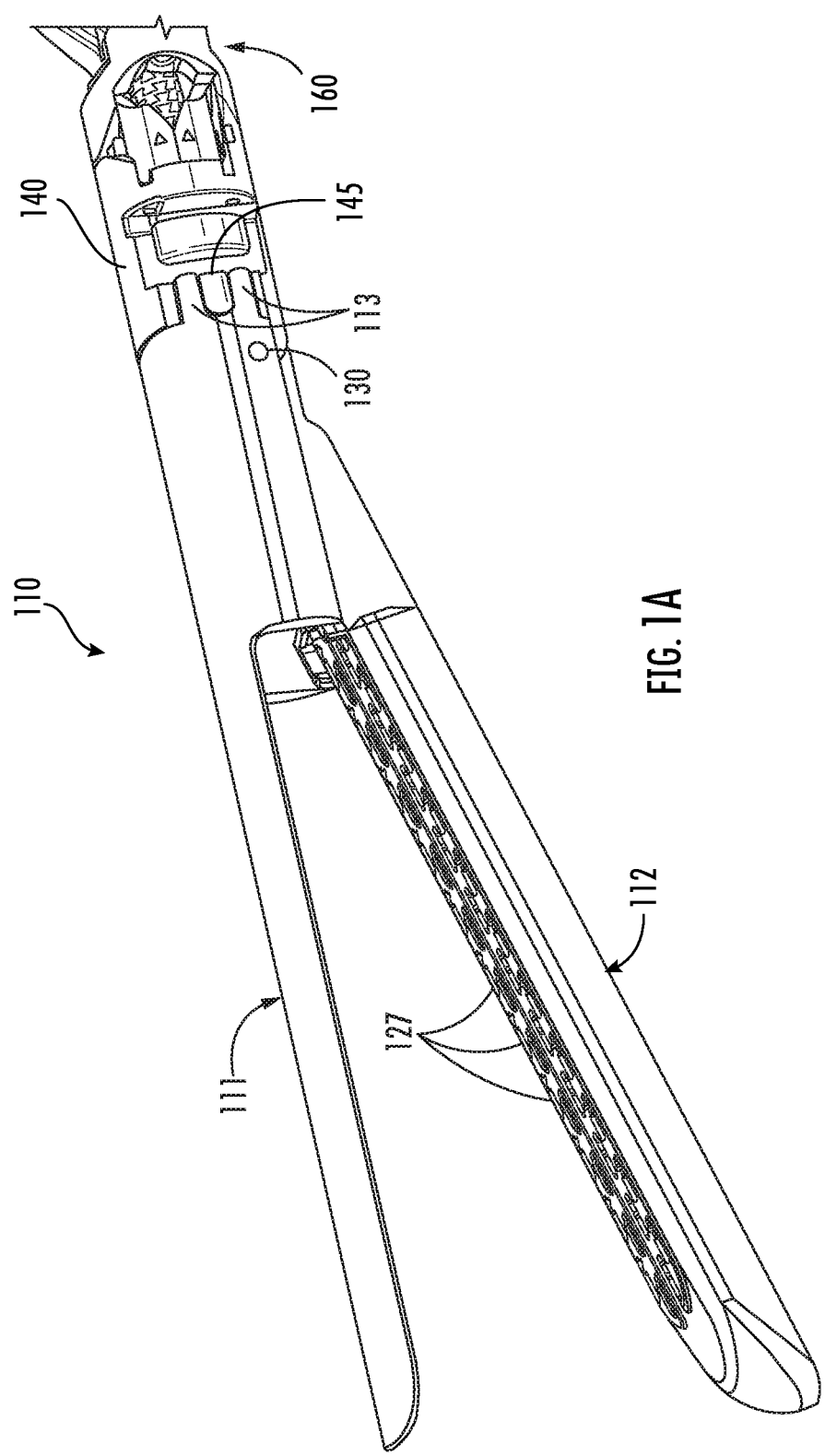
FIG. 1A is a perspective top view of the distal end portion of an illustrative surgical instrument with the jaws in the open position.

FIG. 1A illustrates the distal end portion of surgical instrument 100, including an end effector 110 having first and second jaws 111, 112, a clevis 140 for mounting jaws 111, 112 to the instrument, and an articulation mechanism, such as a wrist 160. First jaw 111 includes an anvil 115 having staple-forming pockets 116 (see FIG. 1D). In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. In the open position, a fresh stapling cartridge 122 (sometimes referred to as a reload and shown more clearly in FIG. 1B) can be loaded into movable jaw 112 and tissue may be positioned between the jaws 111, 112. In the closed position, jaws 111, 112 cooperate to clamp tissue such that cartridge 122 and the anvil 115 are in close cooperative alignment.

Figure 10:
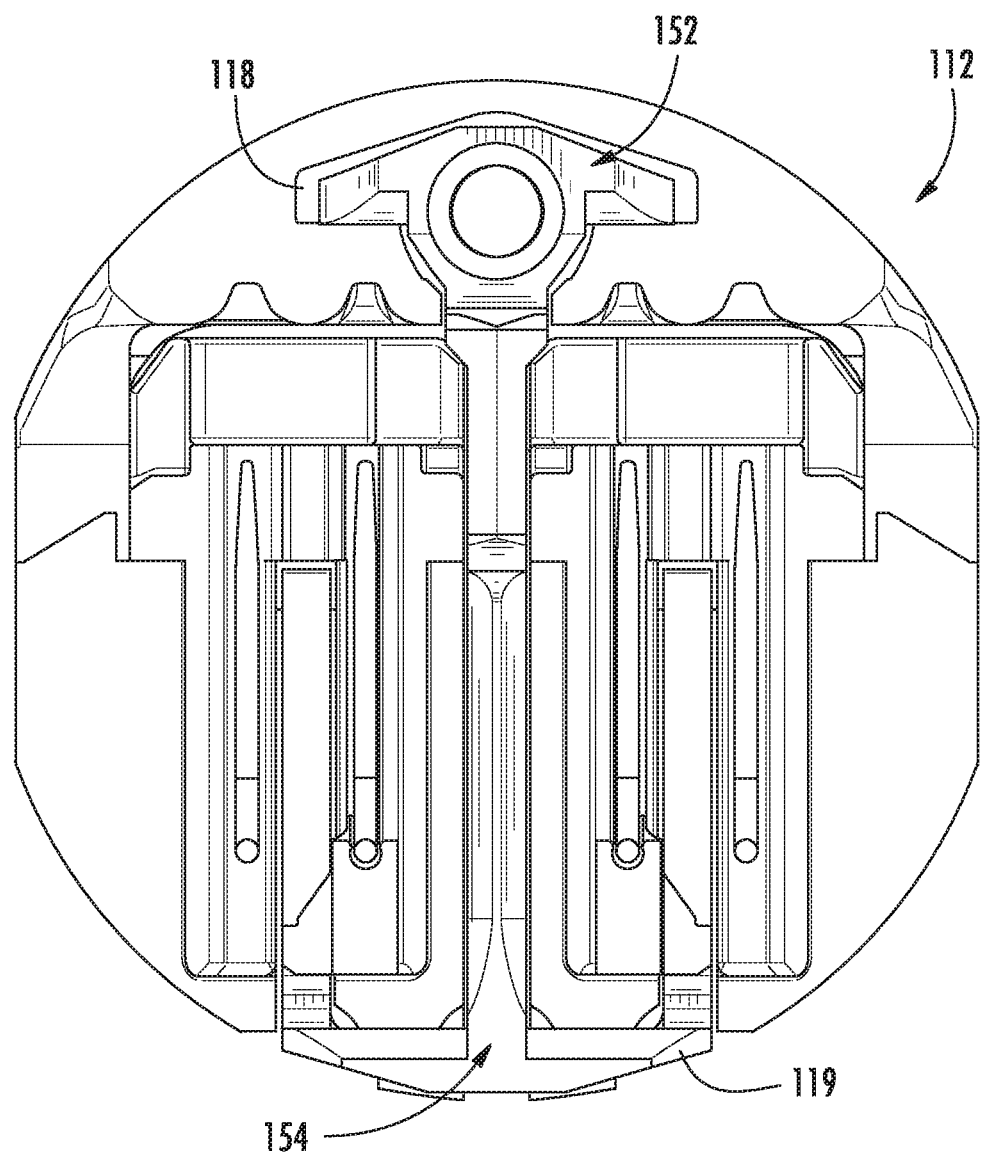
FIG. 10 is a transverse cross-sectional view of a staple cartridge and drive member according to an embodiment of the present disclosure.

Referring now to FIGS. 1B and 10, a representative staple cartridge 122 may include a plurality of staples assemblies, each comprising one or more staples 124 supported on corresponding staple drivers or pushers 126 provided within respective staple apertures 127 formed in cartridge 122. In certain embodiments, staple pusher(s) 126 include one or more supporting elements extending above their top surface for providing support to staples 124 when they are resting thereon. Of course, other suitable geometric designs of staple pusher 126 may be used to receive and hold staple 124 in accordance with the present invention. For example, pusher 126 may have a recess (not shown) for receiving staple 124, as is described in commonly-assigned, provisional patent application Ser. No. 62/855,371, filed May 31, 2019. Alternatively, pusher 126 may have a flatter upper surface (i.e., without a recess or pocket) that allows the backspan of staple 124 to rest thereon, as is described in commonly-assigned, provisional patent application Ser. No. 62/783,460, the complete disclosures of both of these applications are hereby incorporated by reference in their entirety for all purposes.

Figure 1D:
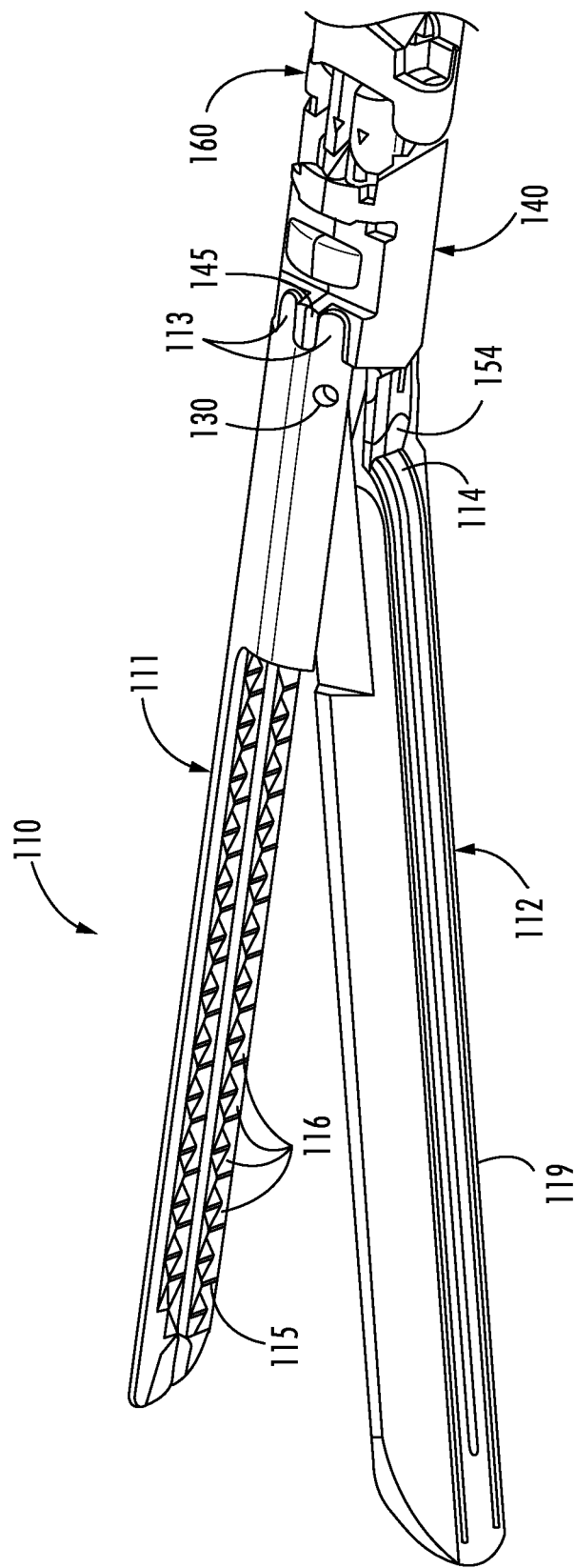
FIG. 1D is a perspective bottom view of the distal end portion of the surgical instrument of FIG. 1A.

In certain embodiments, cartridge 122 also may include a shuttle 123 having an inclined distal surface 125 that, upon distal movement, sequentially acts on staple pushers 126, camming them upwardly, thereby moving staples 124 into deforming contact with anvil 115 (See FIG. 1D). Shuttle 123 may be part of a drive member 150 (FIGS. 7A and 7B) described in more detail below. Cartridge 122 may be removably received within movable jaw 112 or, in single use embodiments, may be manufactured as part of movable jaw 112.

Figure 3:
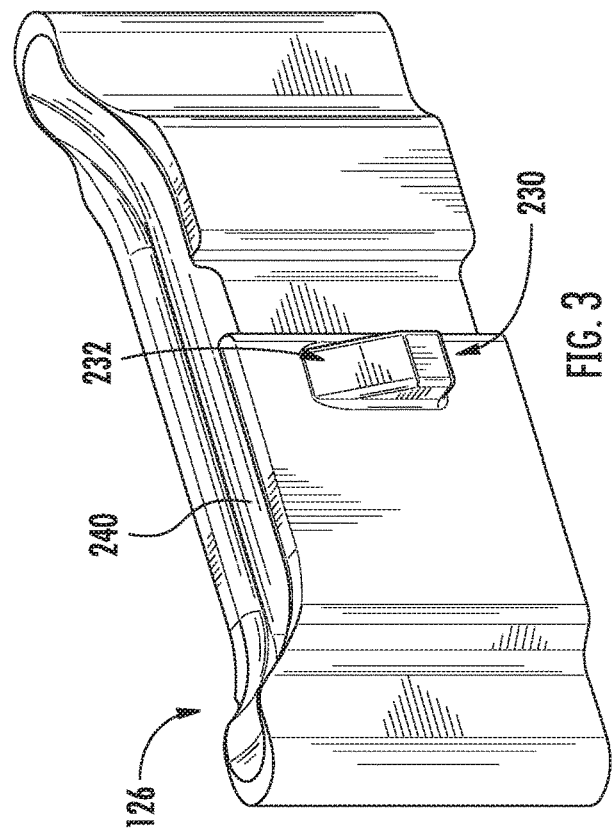
FIG. 3 is a perspective side view of a staple pusher according to certain embodiments of the present disclosure.

FIG. 3 illustrates a preferred embodiment of a staple pusher 126 according to the present invention. As shown, pusher 126 has a projection or retention boss 230 extending laterally outward from pusher 126. Boss 230 preferably has an inclined outer surface 232, the purpose of which will be more fully described below. Pusher 126 further includes a recess or pocket 240 in the top surface of pusher 126 for receiving and holding at least the backspan of a staple 124 (shown in FIGS. 1B and 1C) such that the two legs of staple extend substantially vertically upwards from pusher 126. It will be recognized by those skilled in the art that other suitable geometric designs of staple pusher 126 may be used to receive and hold staple 124. For example, pusher 126 may have a flatter upper surface (i.e., without a recess or pocket) that allows the backspan of staple 124 to rest thereon, as is described in commonly-assigned, provisional patent application No. 62/783,460, the complete disclosure of which is hereby incorporated by reference in its entirety for all purposes.

Figure 2:
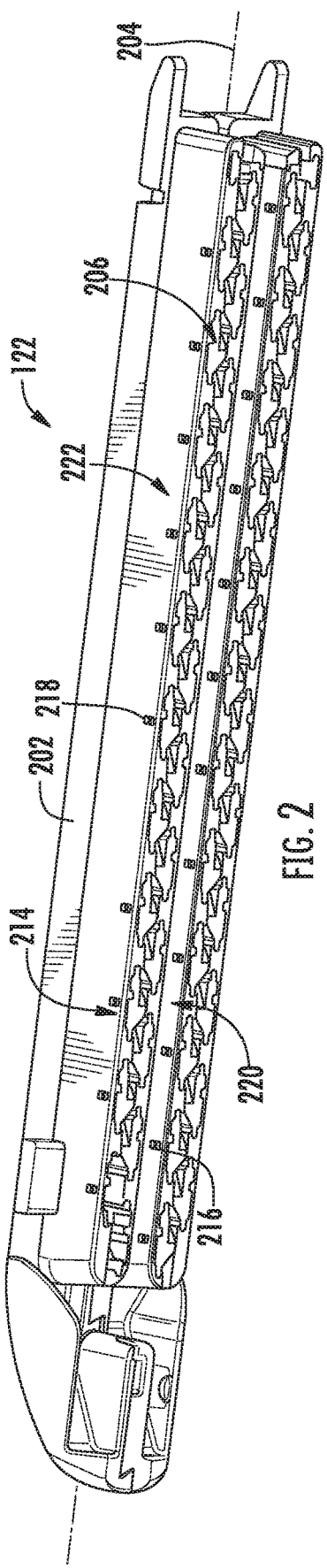
FIG. 2 is a perspective bottom view of a staple cartridge according to certain embodiments of the present disclosure.

Referring now to FIG. 2, a preferred embodiment of staple cartridge 122 will now be described. As shown, cartridge 122 includes a housing 202 extending substantially along a longitudinal axis 204 and including a plurality of compartments 206 that form pockets within the housing to receive the staple assemblies. The staple assemblies each include at least one (preferably 2-4) staple pushers 126 removably coupled to at least one (preferably 2-4) staples 124. The staple assemblies are preferably arranged within compartments 206 such that staple pusher 126 is situated near a bottom surface of housing 202 and staples 124 have their legs facing a top surface of housing 202. For ease of reference, the top surface of housing faces fixed jaw 111 (see FIG. 1). As discussed above, the entire staple cartridge 122 can be loaded into, or permanently affixed to, movable jaw 112 for use in surgery as described in more detail below.

In most conventional staple cartridge designs, the cartridge 122 would also include a sheet metal cover (not shown) surrounding at least a portion of cartridge 122. The cover serves to prevent the staple assemblies from falling out of cartridge 122 prior to use in surgery, e.g., during shipping, handling, etc. The cover, however, adds material thickness to the vertical height and horizontal width of the cartridge. In the present invention, cartridge 122 does not include this cover and, therefore, may be designed with taller staples and/or a smaller overall profile (e.g., diameter) than conventional staple cartridges. In an exemplary embodiment, staple cartridge 122 of the present invention preferably has a diameter less than 12 mm, more preferably about 8 mm. This smaller diameter cartridge allows for the design of a smaller and more compact surgical instrument, which provides the surgeon with more maneuverability during a surgical procedure. In addition, the smaller and more compact surgical instrument is less likely to contact and possibly damage collateral tissue in the surgical arena.

In one embodiment of the present invention, housing 202 of staple cartridge 122 includes a plurality of openings 214 spaced from each other and extending substantially in the direction of longitudinal axis 204. As shown more clearly in FIG. 2, each opening 214 is aligned with one of the staple pushers 126 such that retention boss 230 cooperates with and protrudes through opening 214 (see FIG. 4). Retention boss 230 and opening 214 are sized and configured such that pusher 126 is retained to housing 206 when boss 230 extends through opening 214. During use (described more fully below), inclined outer surface 232 of boss 230 allows pusher 126 to be driven vertically upwards (relative to FIG. 4) by camming surface 232 along the edge of opening 214 as pusher 126 moves upward. Thus, retention boss 230 substantially inhibits movement of pusher 126 relative to housing 206, while allowing for the forced or driven movement (see below) of pusher 126 in one direction only.

The present invention allows the staple assemblies to be retained to housing 202 of staple cartridge 122 without the presence of a conventional sheet metal cover. However, it should be noted that the present invention is not limited to the embodiment described herein and other coupling mechanisms may be used to retain the staple assemblies to the cartridge prior to use. For example, staple pusher 126 and housing 206 may include other cooperating or coupling elements that retain pusher 126 to housing 206 while still allowing it to be driven in one direction by drive member 150, such as interference fits, snap-fit features, press-fit connectors, camming surfaces with various geometries and the like.

As shown in FIG. 2, cartridge 122 preferably includes two rows of staple assemblies extending along longitudinal axis 204. As such, cartridge 122 includes an inner row of openings 216 in an inner wall 220 and an outer row of openings 218 in an outer wall 222 aligned with the respective compartments 206 for staple assemblies 208. To facilitate manufacture of this design (particularly inner row of openings 216), cartridge 122 is formed from two longitudinally shaped sections 224, 226 (shown in FIG. 5A). Sections 224, 226 preferably represent two halves of the overall staple cartridge 122. However, it will be recognized that one of the sections may be larger than the other so long as each section contains one row of openings therein.

Figure 5B:
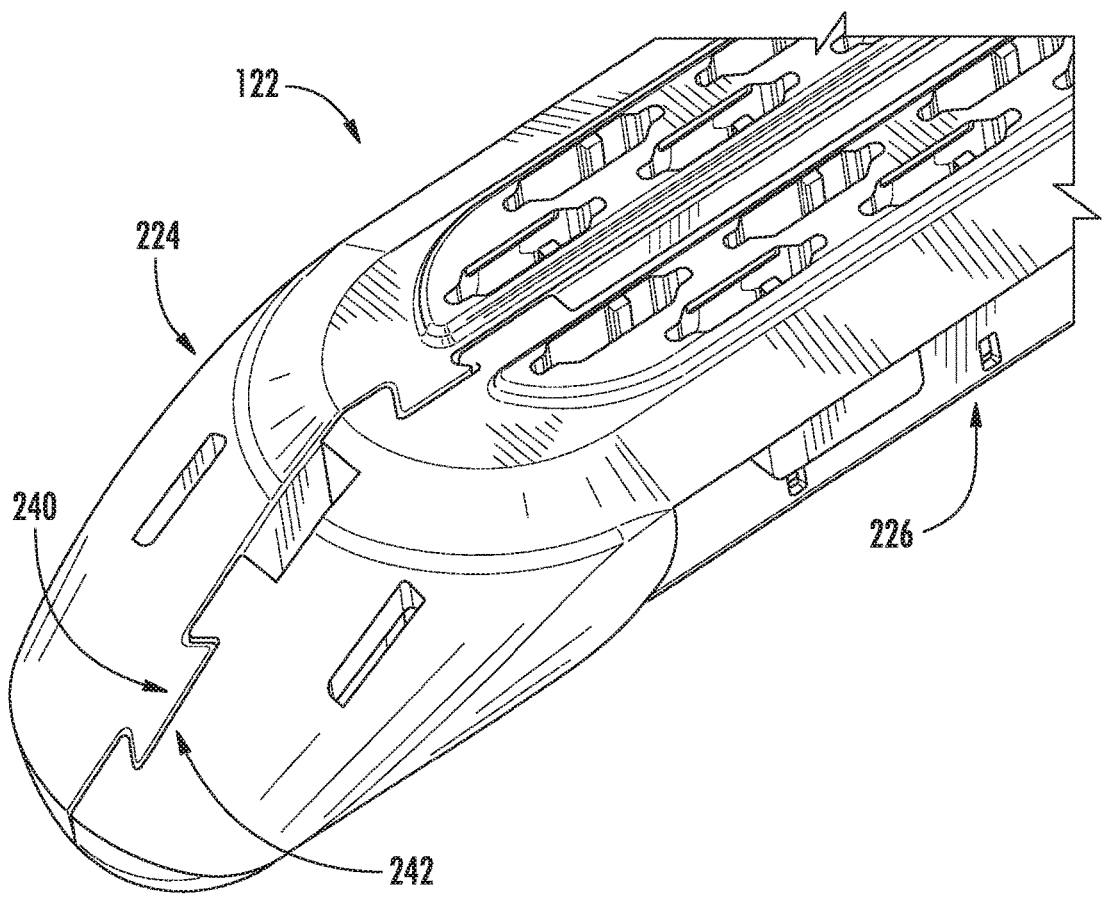
FIG. 5B is a perspective view of a distal end portion of a staple cartridge according to an embodiment of the present disclosure.
Figure 5C:
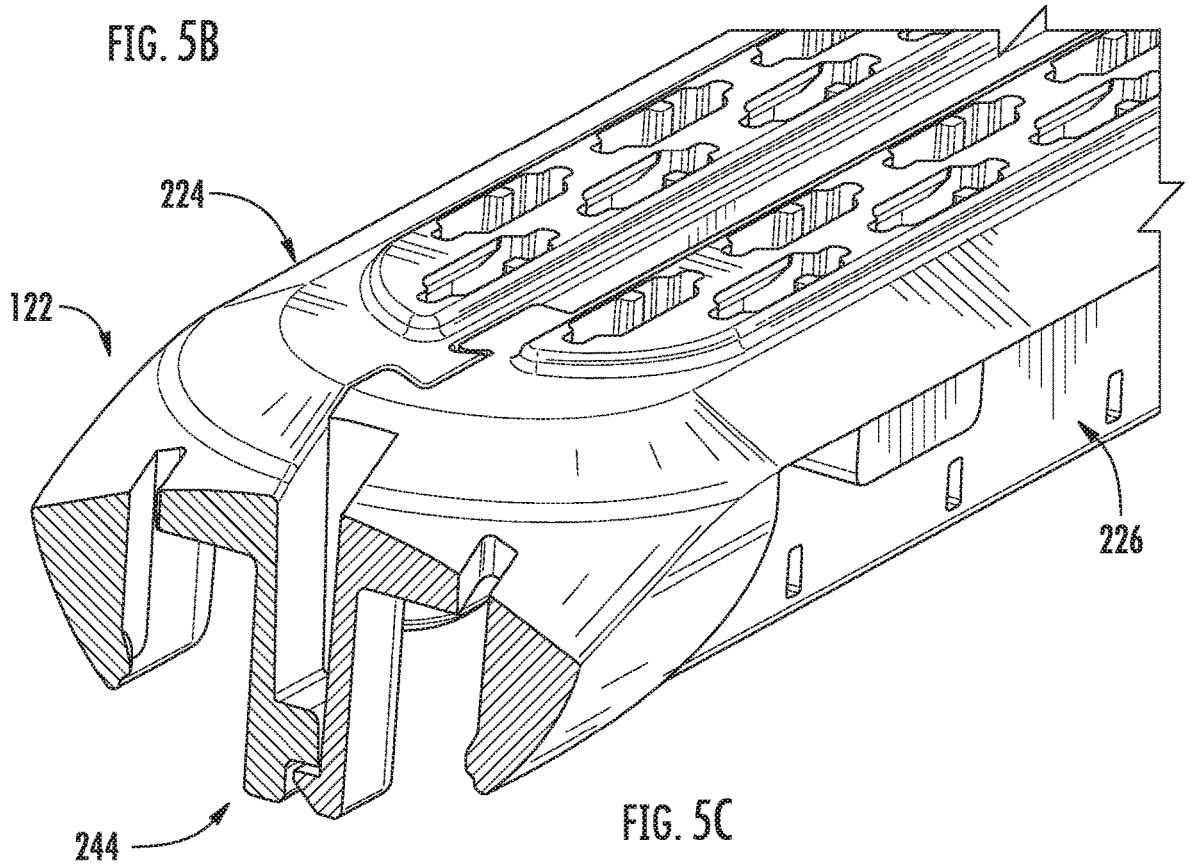
FIG. 5C is a perspective view of a distal end portion of a staple cartridge according to another embodiment of the present disclosure.

Referring now to FIGS. 5B and 5C, the distal portions of sections 224, 226 of cartridge 122 are coupled to each other with coupling elements that hold the two halves of the cartridge together. FIGS. 5B and 5C illustrate preferred embodiments of the coupling elements. As shown in FIG. 5B, section 224 includes male members 240 having a tapered dovetail shape. Section 226 includes the corresponding female members 242 of the tapered dovetail shape. As shown in FIG. 5C, sections 224, 226 may include one or more snap features 244 in addition to, or as an alternative to, male and female members 240, 242. In the preferred embodiment, cartridge 122 will include both features of FIGS. 5B and 5C. In this embodiment, male and female dovetail members 240, 242 fit together to align sections 224, 226 and snap features 244 form a press fit that locks the distal portions of sections 224, 226 together. It should be noted that the present invention is not limited to the coupling elements shown in FIGS. 5B and 5C. For example, other coupled elements may be used with the present invention, such as press-fit connectors, such as solid or compliant press-fit pins and receptacles and other geometries of snap-fit features, such as annular cantilever, torsional, L-shaped, U-shaped and the like.

In certain embodiments, jaws 111, 112 are attached to surgical instrument 100 via a suitable coupling device, such as a clevis 140. Clevis 140 includes upper and lower portions that cooperate when assembled to form a protrusion 145 configured to engage tabs 113 (see FIG. 1A) of jaw 111 to securely mount jaw 111 in a fixed position on instrument 100. Clevis 140 further includes an opening for receiving a pivot pin 130 defining a pivot axis around which jaw 112 pivots as described in more detail below. A more complete description of a suitable clevis 140 for use with the present invention may be found in commonly-assigned, provisional patent application Nos. 62/783,444, filed Dec. 21, 2018; 62/783,481, filed Dec. 21, 2018; 62/783,460, filed Dec. 21, 2018; 62/747,912, filed Oct. 19, 2018; and 62/783,429, filed Dec. 21, 2018, the complete disclosures of which are hereby incorporated by reference in their entirety for all purposes. Of course, it will be recognized by those skilled in the art that other coupling mechanisms known by those skilled in the art may be used with the present invention to attach the jaws 11, 112 to the proximal portion of surgical instrument 100.

Figure 6:
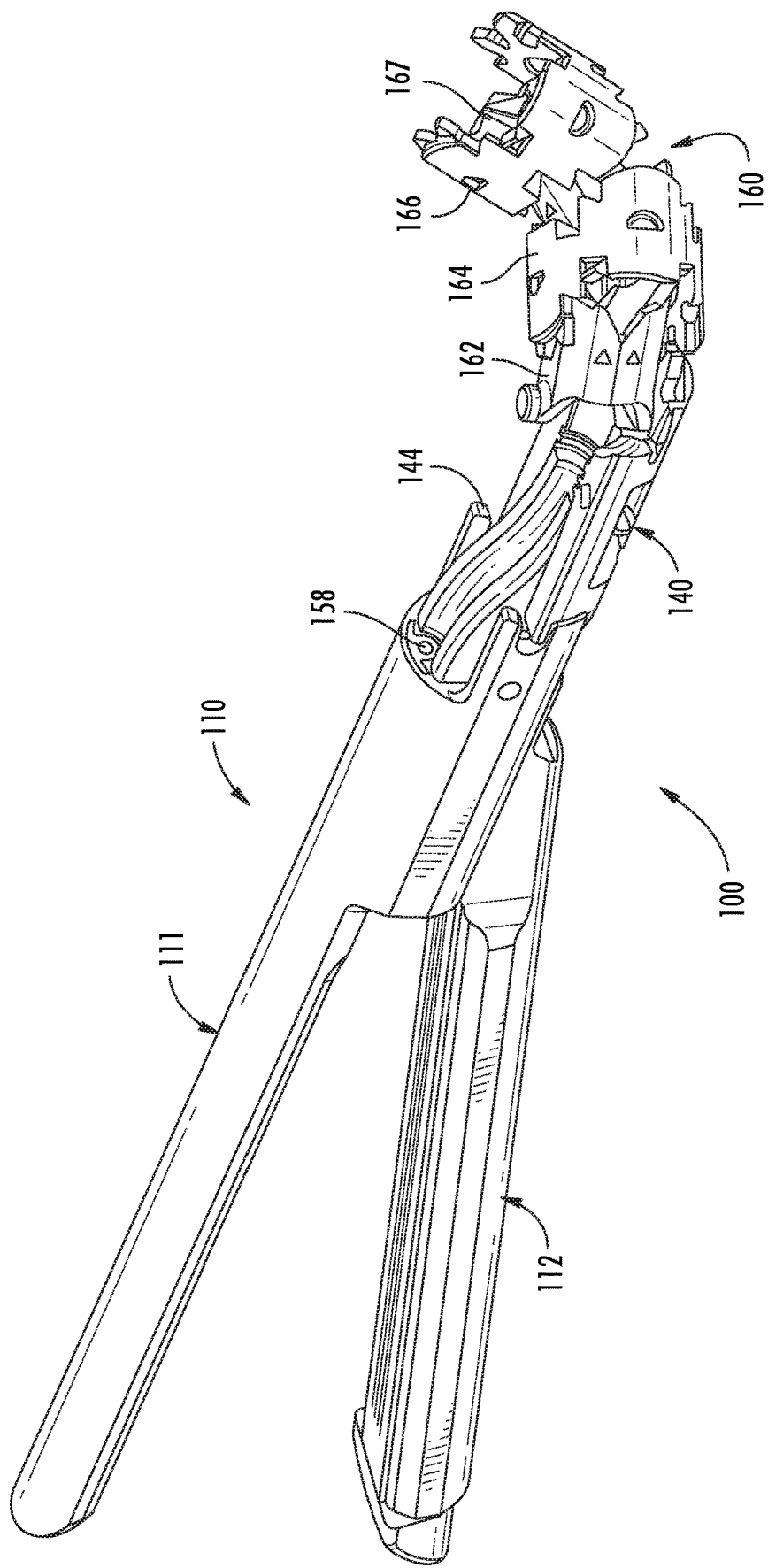
FIG. 6 is a perspective view of the distal end portion of an illustrative surgical instrument with parts removed.
Figure 9:
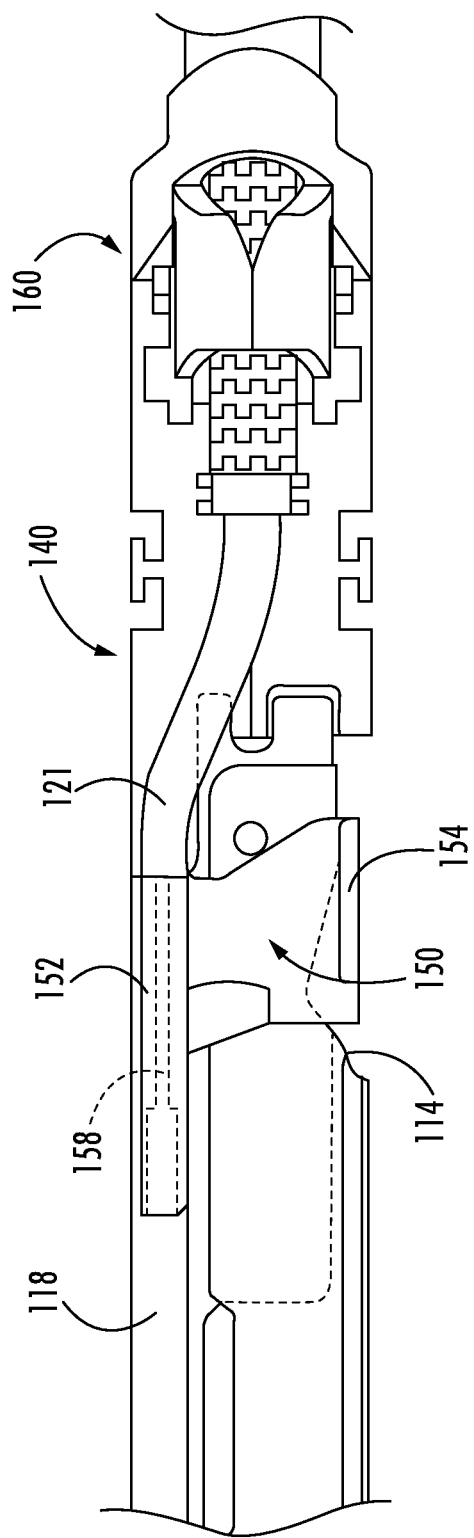
FIG. 9 is a cross-sectional side view of one portion of the illustrative surgical instrument of FIG. 1.

Referring now to FIG. 6, end effector 110 may be articulated in multiple directions by an articulation mechanism. In certain embodiments, the articulation mechanism may be a wrist 160 as shown, although other articulation mechanisms are contemplated. As seen in FIG. 6, a preferred embodiment of wrist 160 includes a plurality of articulation joints 162, 164, 166, etc. that define a bore 167 through which an actuation mechanism (in certain embodiments, coil 120 and drive cable 171, see FIG. 8A) may pass. Upon exiting articulation wrist 160, coil 120 enters and passes through an internal channel (not shown) of clevis 140, ultimately engaging a proximal surface of upper shoe 152 of drive member 150 (see FIG. 8A). Other articulation mechanisms known by those skilled in the art may substitute for wrist 160. Other exemplary articulating mechanisms are shown for example in commonly-assigned, co-pending U.S. Publication. No. 2015/0250530 and International Application No. PCT/US19/62344, filed Nov. 20, 2019 the entire disclosures of which are hereby incorporated by reference in their entirety for all purposes.

As seen in FIGS. 7A and 7B, a preferred embodiment of drive member 150 may include a body, upper shoe 152, lower shoe 154, central portion 156 and lateral portions 159. Lateral portions 159 are the fins that form shuttle 123 shown earlier. Lateral portions 159 of drive member 150 each comprise distal inclined surfaces or ramps 161 that engage with pushers 126 to drive pushers 126 (and the associated staples 124) vertically or perpendicular to longitudinal axis 204 when drive member 150 is translated distally. In a preferred embodiment, shuttle fins 159 are integrated into lower shoe 154 of drive member 150. In conventional designs, this is typically not possible because of the outer sheet metal cover used to retain staple assemblies 208 within housing 202 of staple cartridge 122. Integrating shuttle fins 159 into drive member 150 provides more flexibility in the design of staple cartridge 122. For example, this may allow for a reduction in the size of staple cartridge 122 and surgical instrument 100 and/or increasing the length of staples 124 for a given size of surgical instrument 100.

As shown in FIGS. 8A and 8B, actuation assembly 190 includes a drive cable 171, a coil 120, a sheath 121 surrounding coil 120, and a drive rod 175. Drive cable 171 includes an enlarged distal end 173. Upper shoe 152 of drive member 150 includes a bore 158 into which drive cables 171 are routed. When assembling illustrative surgical instrument 100, coil 120 and protective sheath 121 are slipped over the free end of drive cable 171. The free end of drive cable 171 is attached to drive rod 175 securing coil 120 and the protective sheath 121 between drive member 150 and drive rod 175 as best seen in FIG. 7B). Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITINOL™, poly para-phenyleneterphtalamide materials such as KEVLAR™ commercially available from DuPont. Those of skill in the art may envision other suitable materials.

Enlarged distal end 173 of drive cable 171 resides within an enlarged distal portion 159 of bore 158 in upper shoe 152 of drive member 150, such that a proximal face 157 of enlarged distal end 173 may apply a retraction force on upper shoe 152 when the drive cable 171 is pulled proximally, i.e., in the direction of arrow "B" in FIG. 8B. Drive rod 175 is operationally connected to an actuator (e.g., movable handle 102b), which allows distal translation and proximal retraction of actuation assembly 190. Those skilled in the art will recognize that in a manually actuated instrument, the actuator may be a movable handle, such as moveable handle 102b shown in FIG. 1; in a powered instrument the actuator may be a button (not shown) that causes a motor to act on the drive rod; and in a robotic system, the actuator may be a control device such as the control devices described below in connection with FIG. 12. Any suitable backend actuation mechanism for driving the components of the surgical stapling instrument may be used. For additional details relating to exemplary actuation mechanisms using push/pull drive cables see, e.g., commonly assigned, co-pending International Application WO 2018/049217, the disclosure of which is hereby incorporated by reference in its entirety.

Referring now to FIG. 10, upper shoe 152 of drive member 150 is substantially aligned with and translates through a channel 118 in fixed jaw 111, while lower shoe 154 of drive member 150 is substantially aligned with and translates through a channel 119 and below jaw 112. As shown in FIGS. 8A and 8B, bore 158 is formed through upper shoe 152 to receive drive cable 171 as will be described in more detail below. Proximal surface 153 of upper shoe 152 is configured to be engaged by a coil 120 of actuation assembly 190 such that coil 120 may apply force to upper shoe 152 to advance drive member 150 distally, i.e., in the direction of arrow "A" in FIG. 8B. A knife 128 may be formed on drive member 150 along the distal edge between upper shoe 152 and central portion 156.

During actuation of illustrative surgical instrument 100, drive rod 175 applies force to coil 120, thereby causing coil 120 to apply force to upper shoe 152 of drive member 150, translating it distally (i.e., in the direction of arrow "A" in FIG. 7B) initially closing jaws 111,112 and then ejecting staples 124 from cartridge 122 to staple tissue. After stapling is complete, drive rod 175 applies a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. In certain embodiments, the surgical instrument may be designed such that the drive member 150 is not retracted in the proximal direction after the staples have been fired. One of ordinary skill in the art will appreciate that drive member 150, drive cable 171, and drive rod 175 all move in unison and remain in the same relative position to each other.

In use, in the open configuration, drive member 150 is positioned proximally of cam surface 114 formed on movable jaw 112. As drive member 150 translates in the distal direction, movable jaw 112 will rotate towards the closed position around pivot 117. Once drive member 150 has come into contact with cam surface 114 of movable jaw 112, lower portion 154 of drive member 150 rides underneath cam surface 114, drive member 150 pushes movable jaw 112, causing it to pivot towards the closed position. In the closed position. drive member 150 has translated distally past cam surface 114. In this position, tissue is clamped, and further advancement of the drive member will sever and staple tissue. Of course, it will be recognized by those skilled in the art that drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through a staple cartridge and upper fixed jaw 111 and lower jaw 112 when the surgical stapling instrument is fired (e.g., actuated).

Figure 11:
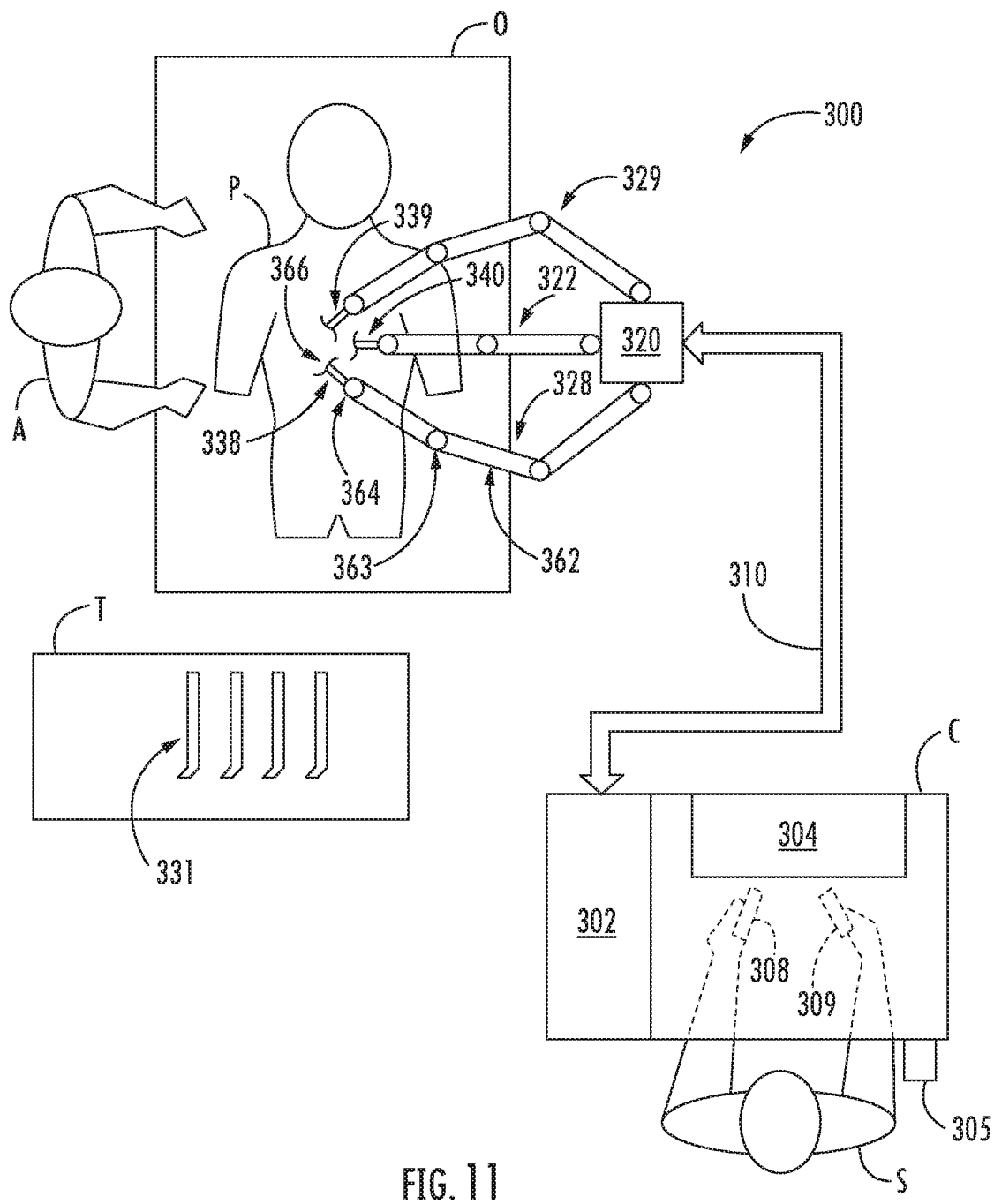
FIG. 11 illustrates a top view of an operating room employing a robotic surgical system utilizing aspects of the present invention.

FIG. 11 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware. For additional details on robotic surgical systems, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are hereby incorporated herein by reference in their entirety for all purposes.

Figure 12:
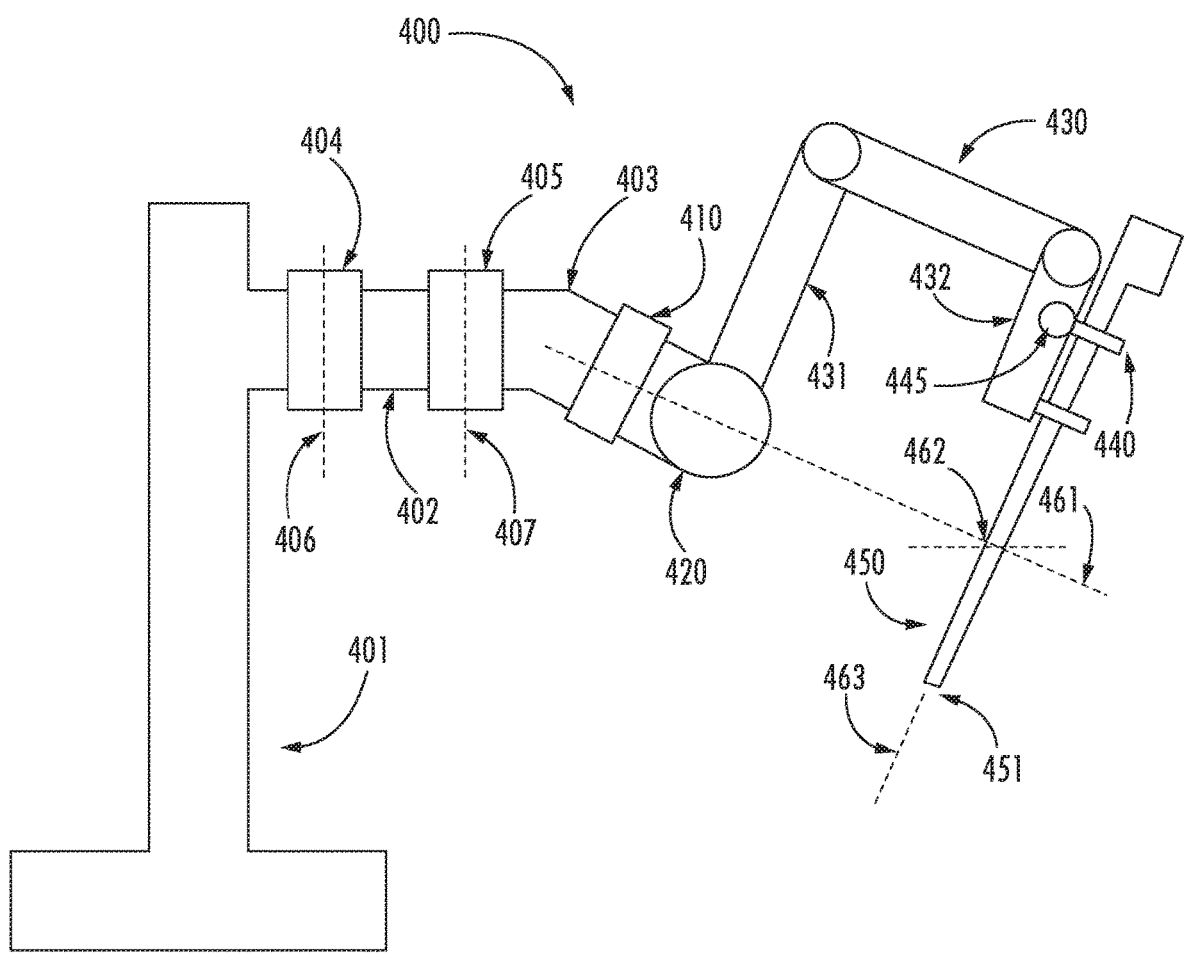
FIG. 12 illustrates a simplified side view of a robotic arm assembly that is usable with various aspects of the present invention.

FIG. 12 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403, which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407. Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator. A more complete description of illustrative robotic surgical systems for use with the present invention can be found in commonly-assigned U.S. Pat. Nos. 9,295,524, 9,339,344, 9,358,074, and 9,452,019, the complete disclosures of which are hereby incorporated by reference in their entirety for all purposes.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A surgical instrument comprising:
an end effector comprising first and second jaws configured to move relative to each other from an open position to a closed position; and
a staple cartridge coupled to one of the first or second jaws and comprising:
a housing comprising a sidewall with an opening, the housing having a longitudinal axis; and
one or more staple assemblies each comprising a staple pusher and a staple, wherein the staple pusher has a projection sized to engage a portion of the housing such that the staple assemblies are retained to the housing, wherein the projection comprises an outer inclined surface, wherein at least a portion of the outer inclined surface extends through the opening in the housing laterally outward, the outer inclined surface being configured to cam along an edge of the opening when forced, the outer inclined surface tapering inward in a direction substantially perpendicular to the longitudinal axis.

2. The surgical instrument of claim 1, wherein the housing has one or more openings spaced from each other substantially along the longitudinal axis.

3. The surgical instrument of claim 1, wherein the staple pusher is detachable from the staple cartridge when forced.

4. The surgical instrument of claim 1, wherein the housing comprises inner and outer wall sections each having a plurality of openings spaced from each other and extending along the longitudinal axis of the housing, the surgical instrument further comprising first and second rows of staple pushers adjacent each other within the housing, wherein each staple pusher has a projection sized to engage with one of the openings in the inner and outer wall sections of the housing to retain each row of staple pushers to the housing.

5. The surgical instrument of claim 1, wherein the housing comprises first and second longitudinal sections coupled to each other, each of the first and second longitudinal sections comprising a wall and a row of openings in the wall extending longitudinally along each section.

6. The surgical instrument of claim 5, wherein the first and second longitudinal sections each comprise a coupling member and wherein the coupling members of each section are configured to cooperate with each other to form an interference fit that couples the sections to each other, wherein the coupling members are disposed on an outer surface of a distal end portion of the longitudinal sections.

7. The surgical instrument of claim 6 further comprising a drive member configured to translate distally through the end effector, the drive member including a central portion and first and second outer portions each having an inclined surface.

8. The surgical instrument of claim 7, wherein the first and second longitudinal sections cooperate to form a channel upon assembly of the first and second portions, the channel being sized to receive the central portion of the drive member.

9. The surgical instrument of claim 8, wherein the inclined surfaces of the outer portions of the drive member are configured to engage the staple pushers upon distal translation of the drive member through the channel of the staple cartridge and move the staples from a first position within an interior of the housing to a second position exterior to the housing.

10. The surgical instrument according to claim 9 further comprising an actuation mechanism in contact with the drive member and configured to translate the drive member distally through the end effector, wherein the actuation mechanism includes a control device of a robotic surgical system.

11. A surgical instrument comprising:
an end effector comprising first and second jaws configured to move relative to each other from an open position to a closed position;
a drive member configured to translate distally through the end effector; and
a staple cartridge coupled to one of the first or second jaws and comprising:
a housing comprising a sidewall with an opening, the housing having a longitudinal axis; and
at least one staple assembly comprising a staple pusher and a staple, wherein the staple pusher comprises a projection configured to retain the staple pusher to the housing and to allow the drive member to force the staple pusher to move relative to the housing in a direction substantially perpendicular to the longitudinal axis, wherein the projection comprises an outer inclined surface, wherein at least a portion of the outer inclined surface extends through the opening in the housing, the outer inclined surface tapering inward in the direction substantially perpendicular to the longitudinal axis and being sized to allow forced movement of the staple pusher in said direction such that said outer inclined surface is cammed along an edge of the opening.

12. The surgical instrument of claim 11, wherein the housing comprises an opening,
wherein the projection is configured to cooperate with the opening to retain the staple pusher to the housing.

13. The surgical instrument of claim 12, wherein the staple pusher is detachable from the staple cartridge upon such forced movement in the direction substantially perpendicular to the longitudinal axis.

14. The surgical instrument according to claim 11, further comprising:
an actuation mechanism in contact with the drive member and configured to translate the drive member distally through the end effector; and
an actuator operatively connected to the actuation mechanism, wherein the actuator includes a control device of a robotic surgical system.

15. A staple cartridge for a surgical instrument comprising:
a housing having a longitudinal axis, a sidewall and one or more openings in the sidewall spaced from each other substantially along the longitudinal axis; and
one or more staple assemblies each comprising a staple pusher and a staple,
wherein each of the staple pushers comprises a projection configured to cooperate with one of the openings in the housing such that the staple assemblies are retained to the housing, wherein each projection comprises an outer inclined surface, wherein at least a portion of the outer inclined surface extends through one of the one or more openings in the housing laterally outward, the outer inclined surface being configured to cam along an edge of the one or more openings when forced, the outer inclined surface tapering inward in a direction substantially perpendicular to the longitudinal axis and being sized to allow forced movement of the staple pusher in said direction.

16. The staple cartridge of claim 15, wherein the inclined surface of the projection is sized to substantially inhibit movement of the staple pusher relative to the sidewall of the housing.

17. The staple cartridge of claim 15, wherein the housing comprises inner and outer wall sections each having a plurality of openings spaced from each other substantially along the longitudinal axis.

18. The staple cartridge of claim 17 further comprising first and second rows of staple assemblies adjacent the respective inner and outer wall sections of the housing.

* * * * *